(12) United States Patent
Pui et al.

(10) Patent No.: US 6,746,869 B2
(45) Date of Patent: Jun. 8, 2004

(54) ELECTROSPRAYING APPARATUS AND METHOD FOR COATING PARTICLES

(75) Inventors: David Y. H. Pui, Plymouth, MN (US); Da-Ren Chen, Creve Coeur, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 61 days.

(21) Appl. No.: 10/162,031

(22) Filed: Jun. 3, 2002

(65) Prior Publication Data

US 2002/0150669 A1 Oct. 17, 2002

Related U.S. Application Data

(60) Continuation of application No. 09/577,747, filed on May 23, 2000, now Pat. No. 6,399,362, which is a division of application No. 09/092,794, filed on Jun. 5, 1998, now Pat. No. 6,093,557.
(60) Provisional application No. 60/049,444, filed on Jun. 12, 1997.

(51) Int. Cl.$^7$ ................................................ C12N 15/88
(52) U.S. Cl. ........................ 435/458; 435/459; 435/470; 435/471; 118/620; 118/303; 239/3; 239/690; 239/706
(58) Field of Search ................................. 435/458, 459, 435/470, 471; 118/620, 303; 239/3, 690, 706

(56) References Cited

U.S. PATENT DOCUMENTS

| | | |
|---|---|---|
| 3,521,125 A | 7/1970 | Nelson |
| 3,608,823 A | 9/1971 | Buschor |
| 3,654,534 A | 4/1972 | Fischer |

(List continued on next page.)

FOREIGN PATENT DOCUMENTS

| | | | |
|---|---|---|---|
| CN | 1052695 | A | 3/1993 |
| DE | 198 46 656 | A1 | 4/1999 |
| DE | 199 09 333 | A1 | 11/1999 |
| EP | 0 234 841 | A2 | 9/1987 |
| EP | 0 270 356 | A2 | 12/1987 |
| EP | 0 258 016 | B1 | 3/1988 |
| EP | 0 258 016 | A1 | 3/1988 |
| EP | 0 434 616 | | 12/1990 |
| EP | 0 429 234 | A3 | 5/1991 |
| EP | 0 429 234 | B1 | 5/1991 |
| EP | 0 429 234 | A2 | 5/1991 |
| EP | 0 434 616 | B1 | 6/1991 |
| EP | 0 434 616 | A1 | 6/1991 |
| JP | 6-242273 | | 9/1994 |
| WO | 91/00915 | | 1/1991 |
| WO | 91/07487 | | 5/1991 |
| WO | 93/07465 | | 4/1993 |
| WO | 98/03267 | | 1/1998 |
| WO | 98/56894 | | 12/1998 |
| WO | 99/30812 | | 6/1999 |
| WO | 99/30835 | | 6/1999 |
| WO | 99/31019 | | 6/1999 |
| WO | 01/87491 | A1 | 11/2001 |

OTHER PUBLICATIONS

Adachi et al., "High–efficiency unipolar aerosol charger using a radioactive alpha source," *Aerosol Science, Industry Health and Environment*, Masuda and Takahashi, eds., Pergamon Press, NY, 1990; 439–441.

Adachi et al., "Unipolar and Bipolar Diffusion Charging of Ultrafine Aerosol Particles," *J. Aerosol Sci.*, 1985; 16(2):109–123.

Büuscher et al., "Performance of a unipolar 'square wave' diffusion charger with variable nt–product," *J. Aerosol Sci.*, 1994; 25(4) 651–663.

Chen et al., "Design and Evaluation of a Nanometer Aerosol Differential Mobility Analyzer (Nano–DMA)," *J. Aerosol Sci.*, 1998; 29(5/6):497–509.

Chen et al., "Electrospraying of Conducting Liquids for Monodisperse Aerosol Generation in the 4nm to 1.8$\mu$m Diameter Range," *J. Aerosol Sci.*, 1995; 26(6):963–977.

Chen et al., "Experimental Investigation of Scaling Laws for Electrospraying: Dielectric Constant Effect," *Aerosol Science and Technology*, 1997; 27(3):367–380.

Fuchs, "On the Stationary Charge Distribution on Aerosol Particles in a Bipolar Ionic Atmosphere," *Geodis:Pura. Appl.*, 1963; 56:185–193.

Ganan–Calvo, "Generation of Steady Liquid Microthreads and Micron–Sized Monodisperse Sprays in Gas Streams," *Phys. Rev. Lett.*, 1998; 80(2) 285–288.

Ganan–Calvo, "New Microfluidic Technologies to Generate Respirable Aerosols for Medical Application," *J. of Aerosol Sci.*, 1999;30(Suppl. 1):S541–S542.

Hoppel et al., "The Nonequililbrium Character of the Aerosol Charge Distribution Produced by Neutralizers," *Aerosol Sci. & Technol.*, 1990; 12:471–496.

Lui et al., "On unipolar diffsion charging of aerosol particles in the continuum regime," *J. Colloid Interface Sci.*, 1977; 58:142–149.

"Minnesota Nanotechnology Summit: Opportunities and Challenges," final program, Mar. 17, 2000, Minneapolis, MN.

(List continued on next page.)

*Primary Examiner*—James Ketter
(74) *Attorney, Agent, or Firm*—Mueting, Raasch & Gebhardt, P.A.

(57) ABSTRACT

An electrospraying apparatus and/or method is used to coat particles. For example, a flow including at least one liquid suspension may be provided through at least one opening at a spray dispenser end. The flow includes at least particles and a coating material. A spray of microdroplets suspending at least the particles is established forward of the spray dispenser end by creating a nonuniform electrical field between the spray dispenser end and an electrode electrically isolated therefrom. The particles are coated with at least a portion of the coating material as the microdroplet evaporates. For example, the suspension may include biological material particles.

17 Claims, 10 Drawing Sheets

U.S. PATENT DOCUMENTS

| | | | |
|---|---|---|---|
| 4,002,777 A | * | 1/1977 | Juvinall et al. ............. 427/483 |
| 4,039,145 A | | 8/1977 | Felici et al. |
| 4,265,641 A | | 5/1981 | Natarajan |
| 4,328,940 A | | 5/1982 | Malcolm |
| 4,414,603 A | | 11/1983 | Masuda |
| 4,476,515 A | | 10/1984 | Coffee |
| 4,578,290 A | | 3/1986 | Komon et al. |
| 4,634,057 A | | 1/1987 | Coffee et al. |
| 4,659,012 A | | 4/1987 | Coffee |
| 4,748,043 A | | 5/1988 | Seaver et al. |
| 4,795,330 A | | 1/1989 | Noakes et al. |
| 4,846,407 A | | 7/1989 | Coffee et al. |
| 4,945,050 A | | 7/1990 | Sanford et al. |
| 5,036,006 A | | 7/1991 | Sanford et al. |
| 5,044,564 A | * | 9/1991 | Sickles .................... 239/690.1 |
| 5,066,587 A | | 11/1991 | Jones et al. |
| 5,100,792 A | | 3/1992 | Sanford et al. |
| 5,120,657 A | | 6/1992 | McCabe et al. |
| 5,141,131 A | | 8/1992 | Miller, Jr. et al. |
| 5,149,655 A | | 9/1992 | McCabe et al. |
| 5,179,022 A | | 1/1993 | Sanford et al. |
| 5,204,253 A | | 4/1993 | Sanford et al. |
| 5,219,746 A | | 6/1993 | Brinegar et al. |
| 5,222,663 A | | 6/1993 | Noakes et al. |
| 5,240,842 A | | 8/1993 | Mets |
| 5,247,842 A | | 9/1993 | Kaufman et al. |
| 5,354,556 A | | 10/1994 | Sparks et al. |
| 5,371,015 A | | 12/1994 | Sanford et al. |
| 5,433,865 A | | 7/1995 | Laurent |
| 5,457,041 A | | 10/1995 | Ginaven et al. |
| 5,475,228 A | | 12/1995 | Palathingal |
| 5,478,744 A | | 12/1995 | Sanford et al. |
| 5,506,125 A | | 4/1996 | McCabe et al. |
| 5,516,670 A | | 5/1996 | Kuehnle et al. |
| 5,525,510 A | | 6/1996 | McCabe et al. |
| 5,584,807 A | | 12/1996 | McCabe |
| 5,621,605 A | | 4/1997 | Inaba et al. |
| 5,655,517 A | | 8/1997 | Coffee |
| 5,683,556 A | | 11/1997 | Nomura et al. |
| 5,685,482 A | * | 11/1997 | Sickles .......................... 239/3 |
| 5,807,436 A | * | 9/1998 | Stachelhaus et al. ........ 118/627 |
| 5,813,614 A | | 9/1998 | Coffee |
| 5,846,595 A | | 12/1998 | Sun et al. |
| 5,866,400 A | | 2/1999 | Palsson et al. |
| 5,873,523 A | | 2/1999 | Gomez et al. |
| 5,915,377 A | | 6/1999 | Coffee |
| 5,973,904 A | | 10/1999 | Pui et al. |
| 5,992,244 A | | 11/1999 | Pui et al. |
| 6,068,199 A | | 5/2000 | Coffee |
| 6,074,688 A | | 6/2000 | Pletcher et al. |
| 6,093,557 A | | 7/2000 | Pui et al. |
| 6,105,571 A | | 8/2000 | Coffee |
| 6,105,877 A | | 8/2000 | Coffee |
| 6,145,391 A | | 11/2000 | Pui et al. |
| 6,252,129 B1 | | 6/2001 | Coffee |
| 6,399,362 B1 | | 6/2002 | Pui et al. |
| 2002/0007869 A1 | | 1/2002 | Pui et al. |

OTHER PUBLICATIONS

Product Literature, BINKS Electrostatic spray painting equipment, 7 pgs, No. Date Provided.

Pui et al., "Nanometer Particles: A New Frontier For Multidisciplinary Research," *J. Aerosol Sci.*, 1997; 28(4) 539–544.

Pui et al., "Unipolar Diffusion Charging Ultrafine Aerosols," *Aerosol Sci. Techn.*, 1988; 8:173–187.

Romay et al., "Free electron charging of ultrafine aerosol particles," *J. Aerosol Sci.*, 1992; 23(7):679–692.

Romay et al., "On the combination coefficient of positive ions with ultrafine neutral particles in the transition and free–molecule regimes," *Aerosol Sci. Techn.*, 1992; 17:134–147.

Romay et al., "Unipolar Diffusion Charging of Aerosol Particles at Low Pressure," *Aerosol Sci. Techn.*, 1991; 15:60–68.

Rulison et al., "Scale–up of electrospray atomization using linear arrays of Taylor cones," *Rev. of Sci. Instrum.*, American Institute of Physics, New York, 1993; 64(3):683–686.

Songstad et al, "Advances in alternative DNA delivery techniques," *Plant Cell, Tissue and Organ Culture*, 1995; 40:1–15.

Wiedensohler et al., "A novel unipolar charger for ultrafine aerosol particles with minimal particles losses," *J. Aerosol Sci.*, 1994; 25(4):639–650.

* cited by examiner

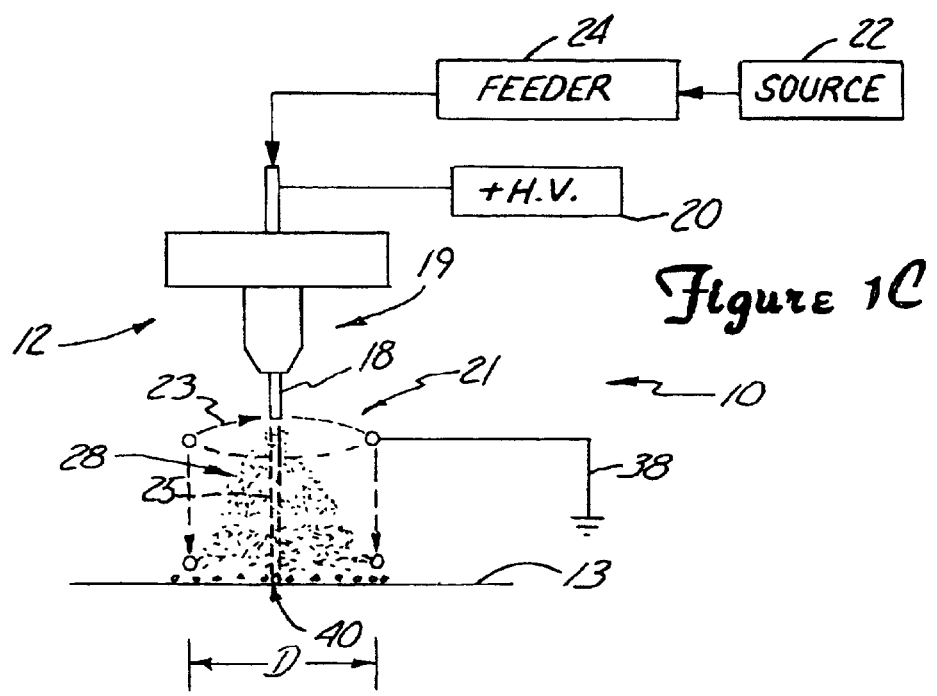

ELECTROSPRAYING APPARATUS AND METHOD FOR COATING PARTICLES

This is a continuation of application Ser. No. 09/577,747, filed May 23, 2000, now U.S. Pat No. 6,399,362, which is a division of application Ser. No. 09/092/794, filed Jun. 5, 1998, now U.S. Pat. No. 6,049,557, which claims the benefit of U.S. Provisional Application Serial No. 60/049,444, filed Jun. 12. 1997, all of which are incorporated herein by reference.

BACKGROUND OF THE INVENTION

Various devices and methods for use in genetic transformation of plant and animal cells have been utilized and many others have been described in various publications. For example, a few early techniques for accomplishing the transport of substances, e.g., DNA, into cells, include uptake mechanisms, fusion mechanisms, and microinjection mechanisms. Generally, uptake mechanisms include the use of substances, such as, for example, liposomes, which encapsulate substances and facilitate transfer of the substances to the cell through fusion of the liposomes with the cell membrane, electroporation, calcium chloride precipitation, and the like. These uptake protocols generally are quite simple and allow for treatment of large numbers of cells at one time, but this technique tends to have a very low efficiency, i.e., transformation frequency is low.

Generally, fusion mechanisms incorporate genetic material into a cell by allowing a cell to fuse with a membrane compatible with the cell membrane of the cell. The fusion of two cells can be used for introducing material into a cell. Cell fusion technologies may have better efficiencies than uptake mechanisms, but cell selection can be more complex, and the resulting cells are typically of elevated ploidy, which makes them of limited use.

Microinjection mechanisms typically employ extremely fine, drawn out capillary tubes, which are sometimes micropipettes or needles. These capillary tubes can be made sufficiently small to be used as syringe needles for the direct injection of biological material into certain types of individual cells. When very small cells are to be injected, very sharp capillary tubes are required, whose tips are very easily broken or clogged. High pressures are required to cause bulk flow through the small orifices and regulation of such flow is difficult. A form of microinjection, commonly referred to as ionophoresis, is also used. Ionophoresis utilizes electrophoresis of substances out of a microelectrode and into a cell, as an alternative to high pressure bulk flow. Although efficiency of microinjection, as one might expect is high, transformation of individual cells is by single cell manipulation and therefore treatment of masses of cells is difficult.

More recently, various techniques involving acceleration of substances for bombardment with cells to accomplish gene transfer have been used and described, e.g., gene guns. For example, such techniques include the use of mechanical impact to project such substances, the use of electrostatic acceleration of the substances, and/or the use of electrostatic discharge to project such substances. It has been stated that such techniques allow the substances to attain a velocity enabling them to penetrate cells.

Various forms of accelerating the substances, for example, are described in the gene gun patent to Sanford et al., U.S. Pat. No. 4,945,050 entitled "Method for Transforming Substances into Living Cells and Tissues and Apparatus Therefor." As described therein, for example, a mechanical shock is applied to a layer of particles (e.g., gold), which are coated, impregnated, or otherwise associated with biological material. The impact causes the particles to be accelerated such that the particles hit the cells to be transformed downstream of the apparatus causing the mechanical shock. The particles puncture the cell membrane and enter the cell, releasing the biological material into the cells.

Spark discharge techniques for accelerating the particles, as described in U.S. Pat. No. 5,120,657 to McCabe et. al., includes the use of a spark discharge chamber. The chamber includes electrodes spaced by a spark gap. A movable particle carrier is moved when a spark discharge in the chamber creates a shock wave that accelerates the movable particle carrier such that the movable particle carrier hits another object accelerating the cells for impact with the target cells to be transformed.

However, such mechanical shock techniques have various disadvantages. First, the techniques are generally batch techniques, i.e., they transfer a certain batch of coated or impregnated particles. If more particles than the number of particles in a single batch are to be transferred, another run or batch must be initiated. For example, this may involve reloading or replacing a part of the apparatus containing the particles, e.g., the movable particle carrier described above.

Further, the coated or impregnated particles when positioned on the transfer surface, e.g., such as the movable particle carrier, may be agglomerated, or such agglomeration may occur during the transfer. Agglomeration of the particles may cause undesirable pit damages to the target cells upon impact therewith.

Yet further, preparation of coated or impregnated particles is a time consuming process. For example, it may take one or more days to precipitate coated or impregnated particles out of a solution containing the carrier particles and the biological material to be transferred.

In addition, the overall process is not easily controlled. For example, there is typically only a limited range of impact velocity which the coated or impregnated particles may attain. The type and origin of the cell can influence the velocity necessary for transformation. Thus, devices that can produce a broader range of impact velocities are desirable. Further, for example, the delivery of particles uniformly to the target cells is not easily controlled. As such, target cells located at certain positions may be damaged more easily than those target cells surrounding. such positions. For example, target cells located at the center of a batch of target cells may be damaged or killed more readily than those in the surrounding target area when bombarded by coated or impregnated particles by conventional batch gene gun devices. This may be at least in part due to the agglomeration of the particles. As the overall process is not easily controlled, the amount of biological material being delivered to the target cells is not readily controllable.

Other acceleration techniques, such as aerosol beam technology, electrostatic acceleration fields, centrifugal techniques, etc. as described in U.S. Pat. No. 4,945,050; International Publication WO 91/00915 entitled "Aerosol Beam Microinjector;" and various and numerous other references, may not include all of the disadvantages as described above with regard to the use of mechanical shock. However, such techniques do not alleviate all of such problems. For example, the aerosol technique may allow for a more continuous transfer method as opposed to a batch method, but still has the associated agglomeration disadvantages.

For the above reasons, there is a need in the art for gene transfer methods and apparatus which reduce the effect of such disadvantages as described above. The present invention overcomes the problems described above, and other problems as will become apparent to one skilled in the art from the detailed description below.

SUMMARY OF THE INVENTION

A method of introducing biological material into cells according to the present invention includes providing one or more target cells and establishing a spray of substantially dispersed particles including biological material. The substantially dispersed particles have an electrical charge applied thereto such that one or more of the substantially dispersed particles of the spray is introduced into one or more of the target cells.

In one embodiment of the method, the step of establishing the spray of substantially dispersed particles includes dispensing a spray of microdroplets suspending particles. The electrical charge is concentrated on the suspended particles as the microdroplets evaporate.

In various embodiments, the suspended particles may include carrier particles having biological material associated with the carrier particles or the suspended particles may be particles of biological material. The spray may also be a charged spray of powdered biological material.

Further, in yet another embodiment, the step of dispensing the spray of microdroplets suspending particles may include creating a nonuniform electrical field between a dispensing tip from which the spray is established and an electrode electrically isolated from the dispensing tip. The substantially dispersed particles may be directed towards the one or more target cells using the electrode isolated from the dispensing tip.

In another embodiment, the space charge effect of the concentrated electrical charge on the substantially dispersed particles of the spray enable one or more of the particles to be introduced into one or more of the target cells. The electrical charge concentrated on a particular particle is in the range of about 80 percent to about 95 percent of a maximum charge that can be held by the microdroplet suspending the particular particle.

Yet further, in another embodiment of the method, the step of establishing a spray of substantially dispersed particles includes establishing a continuous spray of substantially dispersed particles.

An apparatus for introducing biological material into one or more target cells according to the present invention includes a biological material source including at least biological material. The apparatus further includes a dispensing device operably connected to the biological material source to receive at least biological material from the biological material source. The dispensing device provides a spray of substantially dispersed particles of at least the biological material. Further, the spray of substantially dispersed particles has an electrical charge applied thereto such that one or more of the substantially dispersed particles of the spray is introduced into one or more of the target cells.

In one embodiment of the apparatus, the biological material source includes a suspension source. The suspension source includes a suspension of at least biological material. Further, the dispensing device receives the suspension and dispenses a spray of microdroplets suspending particles of at least biological material.

In another embodiment, the dispensing device includes a dispensing tip from which the spray of microdroplets suspending particles is dispensed and an electrode isolated from the dispensing tip. A nonuniform electrical field is created between the dispensing tip and the electrode. Generally, the electrode, e.g., a ring electrode or a conductive target surface, is located at a position relative to the dispensing tip to direct the spray of substantially dispersed particles towards the one or more target cells. The target and the dispensing device may be movable relative to each other, e.g., a distance between the dispensing device and the target may be adjusted.

Another apparatus for introducing biological material into target cells according to the present invention includes a biological material source including a suspension of at least biological material. The apparatus further includes a capillary tube electrode. The capillary tube electrode includes a capillary tube having a first open end and a second open end with the capillary tube operatively connected to the biological material source to receive a flow of the suspension of at least biological material at the first open end thereof. The apparatus further includes an electrode isolated from but positioned in proximity to the second open end of the capillary tube. A nonuniform electrical field is created between the capillary tube electrode and the electrode such that a spray of microdroplets suspending particles of at least biological material is provided from the second end of the capillary tube. Further, upon evaporation of the microdroplets an electrical charge is concentrated on the suspended particles resulting in a charged spray of substantially dispersed particles such that one or more of the substantially dispersed particles of the spray is introduced into one or more of the target cells.

In one embodiment of the apparatus, the capillary tube electrode further includes a casing concentric with at least a portion of the capillary tube between the first and second open ends thereof. The second open end of the capillary tube extends beyond the casing a predetermined distance. The apparatus further includes a gas source providing a gas to be received between the capillary tube and the concentric casing.

Yet another apparatus for introducing biological material into target cells according to the present invention is described. The apparatus includes a biological material source including a suspension of at least biological material and an electrolyte source for providing a solution. The apparatus further includes a capillary tube electrode having a dispensing tip. The capillary tube electrode includes a first capillary tube having a first open end and a second open end with the first capillary tube operatively connected to the biological material source to receive a flow of the suspension of at least biological material at the first open end thereof. The capillary tube electrode further includes a second capillary tube concentric with at least a portion of the first capillary tube. The solution is received in an annular opening defined between the first and second concentric capillary tubes. Yet further, the apparatus includes an electrode isolated from but positioned in proximity to the dispensing tip of the capillary tube electrode. A nonuniform electrical field is created between the capillary tube electrode and the electrode such that a spray of microdroplets suspending particles of at least biological material is provided from the dispensing tip. Upon evaporation of the microdroplets, an electrical charge is concentrated on the suspended particles resulting in a charged spray of substantially dispersed particles.

Another method for introducing biological material into target cells according to the present invention includes providing one or more target cells, providing a first flow of a suspension including at least biological material, and providing a second flow of electrolyte solution. A spray of substantially dispersed particles including at least biological material is established from the first flow and the second flow. The substantially dispersed particles have an electrical charge applied thereto such that one or more of the substantially dispersed particles of the spray is introduced into one or more of the target cells.

BRIEF DESCRIPTION OF THE DRAWINGS

FIG. 1C is one embodiment of the electrospraying apparatus of FIG. 1B in accordance with the present invention for establishing a charged spray using a capillary tube electrode and a biological material source including a suspension.

DETAILED DESCRIPTION OF THE EMBODIMENTS

Figure 1A:
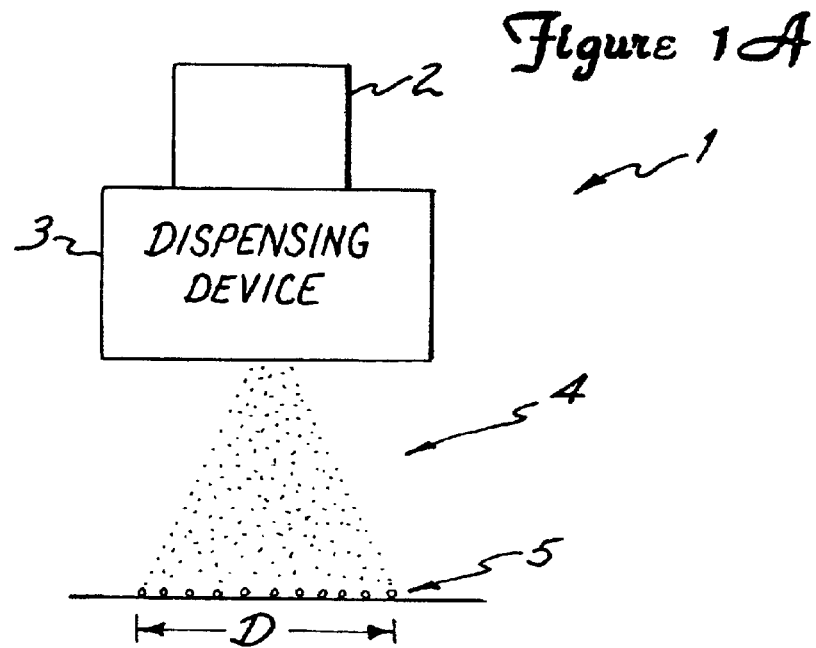
FIG. 1A is a general block diagram representative of an electrospraying apparatus in accordance with the present invention for establishing a charged spray using a biological material source.

The present invention shall first generally be described with reference to FIGS. 1A–1C. Various other embodiments of the present invention shall then be described further with reference to FIGS. 2–9. It will become apparent to one skilled in the art that elements from one embodiment may be used in combination with elements of the other embodiments and that the present invention is not limited to the specific embodiments described herein but only as described in the accompanying claims.

The present invention is directed to apparatus and methods for introduction of biological materials, such as, for example, DNA, into target cells, e.g., plant or animal cells. As shown in FIG. 1A, the present invention uses an electrospraying apparatus 1 to establish a spray 4 of charged particles. The electrospraying apparatus 1 includes a dispensing device 3 which receives at least biological material from a biological material source 2 and establishes the charged spray 4 forward thereof. The space charge effect of the charged particles of the spray 4 enable the particles to attain a velocity such that the particles forcibly contact, and preferably, penetrate target cells 5 when impacted.

As used herein the term charged spray 4 shall refer to a spray of particles having a charge applied thereto established from a source of biological material 2. The source of biological material may be a source of dry biological material alone or biological material associated with carrier particles, i.e., a powdered form of biological material. Preferably, the source of biological material 2 is a suspension of biological material, i.e., a solution including at least biological material. For example, the suspension of biological material may be a suspension of biological material alone or a suspension of biological material and carrier particles. However, any source of biological material which can be sprayed with a unipolar charge (i.e., a same polarity charge) applied thereto can be used according to the present invention.

The dispensing device 3 may be any device for establishing a spray of charge particles 4 with a unipolar charge applied thereto such that the space charge effect of the charged particles of the spray 4 enable the particles to attain a velocity allowing the particles to forcibly contact, and preferably, penetrate the target cells 5. The configuration of the dispensing device 3 will depend at least upon the type of biological material source 2 used. For example, when the biological material source 2 is a source of dry biological material alone or biological material associated with carrier particles, i.e., a powdered form of biological material, the dispensing device 3 may take the form of a spraying device which applies a unipolar charge to the particles of the spray using corona discharge. Such a spraying device may include a structure having an orifice therethrough. A flow of the powdered material may be provided through the orifice, e.g., by way of a pressurized gas source. Upon exit from the orifice, the particles of the spray may be subjected to a weak corona established by brushes positioned about the orifice. One skilled in the art will recognize that this is just one illustrative example of a device for spraying powdered biological material with a charge applied thereto and that the present invention is clearly not limited to this particular embodiment but is limited only as described in the accompanying claims.

As one skilled in the art will recognize, as used herein, the term applied charge refers to applying a unipolar charge (e.g., the same polarity charge) to the particles of spray 4. For example, the charge may be applied by corona discharge as described above with reference to powdered biological material. Further, for example, the charge may be applied by concentration of charge on the spray of particles through evaporation of solution suspending the particles in an established electrical field as further described below with respect to the general illustration of FIG. 1B. In other words, for example, the biological material source 2 is a suspension of biological material and a spray of microdroplets is dispensed from the dispensing device 3, i.e., particles suspended by microdroplets are dispensed. The particles suspended by microdroplets may be carrier particles and biological material or biological material itself without the use of carrier particles. In other words, when dispensed, the spray is preferably a spray of liquid suspended particles as opposed to a powder spray. The liquid portion of the spray of suspended particles generally evaporates to concentrate the charge of the liquid portion on the particles resulting in a spray of charged particles as will be described further below with reference to FIG. 1B.

The spray of particles provided by electrospraying provides for a controllable biological material transfer process which is not limited to batch processing. Rather, the electrospray technique may be utilized in a continuous manner.

The electrospraying mechanism 1 provides a charged spray with a high concentration of charged particles. Preferably, the concentration of charged particles in the spray is in the range of about $10^5$ particles/cubic centimeter (particles/cc) to about $10^{12}$ particles/cc; more preferably in range of about $10^7$ particles/cc to about $10^5$ particles/cc; and further even more preferably about $10^9$ particles/cc. Below about $10^5$ particles/cc, the concentration of charged particles is to low for the space charge effect to attain a velocity for introduction into most target cells. Due to the space charge effect, i.e., the effect created by the charge repulsion of charged particles, a spray of substantially dispersed particles having the same polarity charge is provided with the particles distributed substantially uniformly across the spray area (e.g., the area represented by D in FIG. 1A) wherein the target cells are placed. As used herein, the term substantially dispersed particles refers to uniformly and/or nonuniformly sized particles separated by an applied repulsive electrostatic force. Thus, the electrospray process is a consistent and reproducible transfer process. Further, because the charged particles of the spray repel from one another, agglomeration of the particles is avoided. As such, the electrospray technology provides for reduced cell pit damage and shock injury which are common results when particle agglomeration occurs utilizing conventional methods of transfer. In addition, as described below, the electrospraying technique allows the gene transfer process to be controlled in various manners.

Due to the small size of the charged particles of the spray established in the region of a target including one or more cells, the space charge effect, i.e., the effect created by the charge repulsion of charged particles, provides particles having sufficient velocity to forcibly contact, and preferably penetrate, one or more target cells. However, such space charge effect also creates a spray of charged particles that is generally not contained, i.e., the particles randomly disperse in multiple directions. Therefore, it is preferable to confine or direct the spray of charged particles towards the one or more target cells. As illustrated below, one technique of providing such containment and/or direction for such charged particles is to use an electrode already required to establish the charged spray when the biological material source is a suspension of at least biological material. In other words, the electrode is used to provide a nonuniform electric field for establishing a charged spray and also provides direction for the particles of the charged spray as is described further below.

Figure 1B:
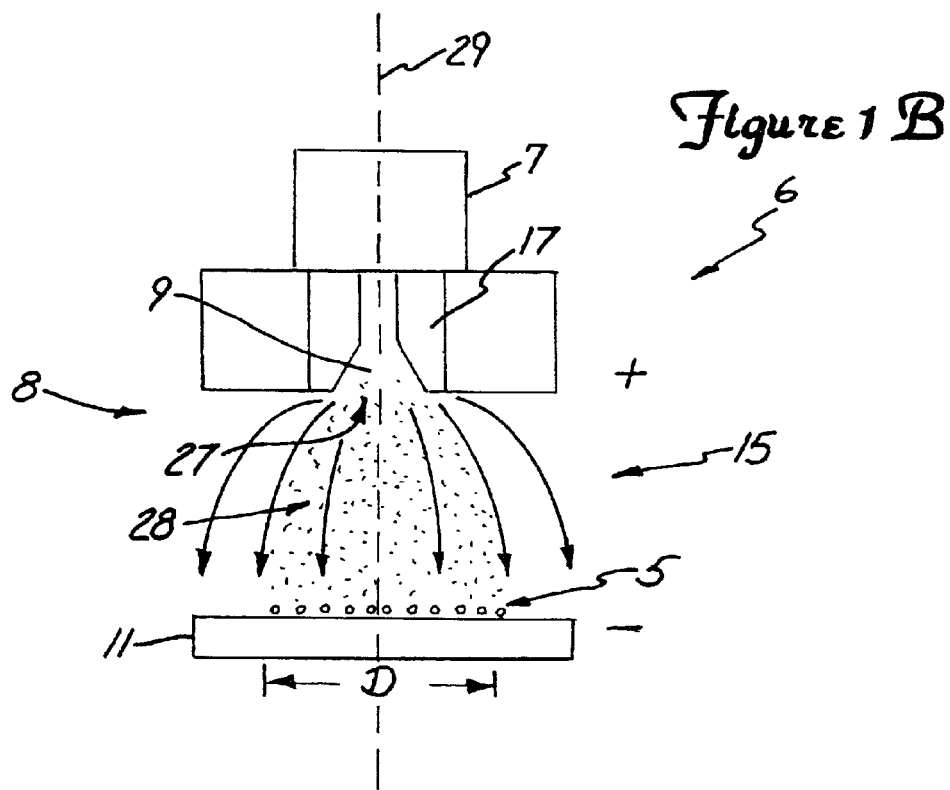
FIG. 1B is a general diagrammatical illustration of an electrospraying apparatus in accordance with the present invention for establishing a charged spray using a biological material source including a suspension.

FIG. 1B generally shows a diagrammatical illustration of an electrospraying apparatus 6 for establishing a charged spray 28 using a dispensing device 8 which receives a flow of a suspension from a biological material source 7. The biological material source 7 contains a suspension of at least biological material, e.g., biological material alone or biological material and carrier particles. Generally, the dispensing device 8 includes a conductive structure 17 defining an orifice 9 (e.g., a capillary tube, an orifice defined in a flooding chamber, etc.) for receiving a flow of solution suspending particles, e.g., biological material alone or carrier particles along with biological material. For example, the solution may be pushed or pulled through the orifice 9 at dispensing tip 27 of the conductive structure 17 defining the orifice 9, e.g., pushed by a pump. The conductive structure 17 defining the orifice 9 functions as a first electrode of the dispensing device 8 with the dispensing tip 27 of the conductive structure positioned for dispensing microdroplets towards target cells 5. Further the dispensing device 8 includes a second electrode structure 11. An electrical potential difference is applied between the first electrode 17 and second electrode 11 to create a nonuniform electric field between the first electrode 17 and second electrode 11. One skilled in the art will recognize that the electrodes may be formed using one or more conductive elements.

Generally, in operation, a flow of the suspension is provided through the orifice 9, e.g., pushed and/or pulled through the orifice 9. A meniscus is formed at the dispensing tip 27 where the orifice 9 has a diameter in the preferred range of about 6 microns to about 2 millimeters (mm). A potential difference is applied to establish a nonuniform field 15 between the first electrode 17 and second electrode 11. For example, a high positive voltage may be applied to the first electrode 17 with the second electrode 11 being grounded. Further, for example, a voltage difference in the preferred range of about 2000 volts to about 6000 volts may be applied.

As used herein, nonuniform electric field refers to an electric field created by an electrical potential difference between two electrodes. The nonuniform electric field includes at least some electric field lines that are more locally concentrated at one electrode relative to the other electrode, e.g., more concentrated at the dispensing tip relative to the second electrode. In other words, for example, at least some of the field lines are off-axis relative to a longitudinal axis 29 through the center of the orifice 9. Further, for example, the electrode 11 is positioned forward of the dispensing tip 27 towards the target cells 5 and the electrode 11 is of a size and/or includes at least a portion that is located at a position away from the longitudinal axis 29. Yet further, for example, the electrode 11 may be a ring electrode having a diameter larger than the diameter of the orifice 9 and positioned forward of the dispensing tip 27 with an axis through the center of the ring electrode coincident with the longitudinal axis 29 of the orifice 9. Further, for example, the electrode 11 may be a conductive target surface having an area greater than a cross section area taken through the orifice 9 perpendicular to the longitudinal axis 29 and positioned forward of the dispensing tip 27.

In the case where the biological material source 7 is a suspension of biological material (without the use of carrier particles), the suspension is flowed (e.g., pushed and/or pulled) through the orifice 9. Generally, the liquid portion of the suspension provided to the orifice 9 has an electrical conductivity. The biological material generally has a small charge associated therewith, e.g., DNA may have a small negative charge, but the charge of the biological material is inconsequential due to the larger charge concentrated on the biological material as described below.

As the suspension progresses through the orifice, the potential difference between the first and second electrodes which creates the electrical field therebetween strips the liquid of one polarity of charge, i.e., the negative charge is stripped when a high positive voltage is applied to the electrode 17, leaving a positively charged microdroplet to be dispensed from the dispensing tip 27. For example, the meniscus at the dispensing tip may form a cone jet for dispensing a spray of microdroplets suspending biological material when the forces of the nonuniform field 15 balances the surface tension of the meniscus. The spray of microdroplets further become more positive in the nonuniform electric field 15.

As the microdroplets evaporate, the charge of the microdroplets concentrate on the biological material resulting in a spray of charged biological material particles. The amount of charge on the microdroplet, and thus the amount of charge on a particle after evaporation, is based at least upon the conductivity of the liquid used to spray the microdroplets, the surface tension of the liquid, the dielectric constant of the liquid, and the feed flow rate of the liquid. Generally, the space charge effect due to the concentrated electrical charge on the substantially dispersed particles of the spray enable the particles to forcibly contact, and preferably, penetrate the target cells. The electrical charge concentrated on a particular particle is preferably in the range of about 80 percent to about 95 percent of a maximum charge that can be held by the microdroplet suspending the particular particle, e.g., biological material particle, without the microdroplet being shattered or torn apart, i.e., in the range of about 80 percent to about 95 percent of the Rayleigh charge limit. At 100 percent, the surface tension of the microdroplet is overcome by the electrical forces causing droplet disintegration. The nonuniform electrical field also provides for containment of the particles and/or direction for the particles which would otherwise proceed in random directions due to the space charge effect.

In the case where the biological material source 7 is a suspension of biological material and carrier particles, the suspension is flowed (e.g., pushed or pulled) through the orifice 9. Generally, the liquid portion of the suspension provided to the orifice 9 has an electrical conductivity. As will be described below, more than one flow of solution may be used to establish the spray. For example, one flow of material may be a suspension of material using deionized water with a second flow of material including an electrolyte solution having a suitable conductivity. The biological material generally has a small but inconsequential charge associated therewith. The carrier particles are generally neutral.

As the suspension progresses through the orifice, the potential difference between the first and second electrodes which creates the nonuniform electrical field therebetween strips the liquid of one polarity of charge, i.e., the negative charge is stripped when a high positive voltage is applied to the electrode 17, leaving a positively charged microdroplet to be dispensed from the dispensing tip 27. A spray of microdroplets suspending biological material and carrier particles is established forward of the dispensing tip 27 with the microdroplets being positively charged.

As the microdroplets evaporate, the charge of the microdroplets concentrate on the biological material and carrier particles resulting in a spray of positively charged carrier particles associated with biological material. The biological material, which may carry a slightly negative charge, are attracted to the positively charged carrier particles resulting in better adhesion between the biological material and the carrier particles. This is unlike conventionally prepared carrier particles having associated biological material because in conventional processes the neutral carrier particles do not create such attraction forces with the slightly negatively charged biological material. In other words, the present invention provides a better coating process for coating carrier particles with biological material. This results in more uniform distribution of biological material being delivered to the target cells. Generally, as described above, the space charge effect due to the concentrated electrical charge on the substantially dispersed particles of the spray enable the particles to forcible contact, and preferably, penetrate the target cells.

One skilled in the art will recognize that the voltages applied may be reversed. For example, the first electrode may be grounded with a high positive voltage applied to the second electrode. In such a case, the particles of the spray would have a negative charge concentrated thereon. Further, any other applied voltage configuration providing a nonuniform electrical field to establish the charged spray of particles may be used.

Further, one skilled in the art will recognize that the spray of particles need not have the biological material associated with the carrier particles. For example, if a positive voltage is applied to the second electrode 11 and the first electrode 17 is grounded, then the carrier particles which are normally neutral in the suspension will have a negative charge thereon as they are spray. With biological material being slightly negative, repulsion forces may keep the carrier particles separated from the biological material and therefore unassociated therefrom. In such a manner, for example, the carrier particles and the biological material particles would be separate from one another in the spray of charged particles. The carrier particles may penetrate the target cells first forming a channel in the target cells such that the biological material particles may easily travel therethrough for introduction into the target cells.

One generalized embodiment of the electrospray apparatus 6 shown generally in FIG. 1B shall be described with reference to the electrospraying apparatus 10 shown in FIG. 1C. Generally, the electrospraying apparatus 10 in accordance with the present invention includes an electrospray dispensing device 12 positioned for providing a charged spray 28. Downstream from or forward of the dispensing device 12 is positioned a target 13 including one or more target cells 40.

In accordance with the present invention, the spray 28 has an electrical charge applied thereto by way of a high positive voltage source 20 applied to a capillary tube electrode 18 of distributor head 19 of the electrospray dispensing device 12 and the electrode 21 being connected to ground 38. The spray 28 is established as described above with use of the nonuniform electric field created between the dispensing tip 23 of the capillary tube electrode 18 and the electrode 21. The spray 28 may be provided by any electrospray dispensing device suitable for providing a spray 28 having a charge applied thereto. Preferably, the charge of the particles is adequate for enabling the particles of the spray 28 to have a velocity due to space charge effect sufficient for the dispersed particles of the spray 28 to penetrate target cells 40.

The particle velocity is primarily a function of the particle charge and the space charge effect. The nonuniform electric field formed between the high voltage capillary tube electrode 18 and the electrically grounded electrode 21 provides for the dispensing of the spray 28 from the dispensing tip 23 of distributor head 19. As described below, depending upon the potential difference applied between the distributor head 19 having a first electrode, e.g., capillary tube electrode 18, and the second electrode 21, different modes of spray operation can be established.

The nonuniform electric field can be provided by various configurations. For example, the second electrode 21 may be any conductive material grounded and positioned to establish the formation of a spray 28 from the dispensing tip 23 of the distributor head 19 or otherwise causing the provision of a charged spray from the distributor head 19, e.g., the second electrode may be a grounded ring electrode, a grounded target surface holding the cells, etc. The second electrode 21 may be located at various positions as shown in FIG. 1C. For example, the electrode 21 may be located at a position just forward of the distributor head 19, or the electrode 21 may be located further away from the distributor head 19 closer to the target cells 40.

It will be recognized that the second electrode 21 may take one of many different configurations. For example, the electrode may be a conductive platform upon which the cells are positioned. Further, for example, the electrode 21 may be a ring electrode having an axis coincident with an axis of distributor head 19, etc. For the electric field to be nonuniform, at least one portion of the electrode 21 must be positioned outside of a hypothetical cylinder 25 extending from the perimeter of the capillary tube electrode to target 13. In other words, electric field lines must extend to and/or from an area outside of the hypothetical cylinder 25.

The strength of the field may be adjusted by adjustment of the distance between the first electrode 18 and second electrode 21. The farther the electrode 21 is from the distributor head 19, the lesser the field strength. However, with such increasing distance, more directionality is provided for the spray 28. For example, if the second electrode 21 is close to the distributor head 19, the space charge effect will cause the particles to disperse into a relatively large area D. On the other hand, the particles can be directed to various targets by moving the electrode 21 to various positions. For example, the electrode 21, e.g., a ring electrode, can be moved close to the target cells 40 to provide a uniform spray 28 in the area proximate thereto.

The source 22 which provides biological material to feeder 24 may be one of many types of biological material sources. Source 22 may be a liquid suspension including biological material. Further, the liquid suspension may include a liquid suspension of bulk biological material (i.e., without carrier particles), may be a liquid suspension of carrier particles and biological material, or may be a liquid suspension of carrier particles having biological material associated therewith, e.g., carrier particles coated or impregnated with DNA.

The present invention hereinafter shall primarily be described with reference to use of a source 22 that is a suspension of carrier particles and biological material, e.g., DNA and gold particle suspension. However, even though the description is focused to the use of a carrier particle suspension, the benefits of the present invention are clearly applicable when other sources are used for providing charged sprays as described herein. It will be recognized that carrier particles of the suspension of carrier particles and biological matter need not be coated with the biological material prior to preparing and using the suspension. In other words, generally, such a suspension is created by mixing the carrier particles and biological material into the suspension liquid, e.g., buffer, electrolyte solution, deionized water, etc. This generally eliminates the substantially time consuming conventional preparatory processes involved in coating or impregnating carrier particles for use in conventional batch gene gun devices.

The suspension may include any liquids suitable for biological material delivery. Further, a component of calcium chloride may be used in the liquid. Any solutions which are suitable for raising cells, such as nutriant solutions, may also be used. Further, for example, the liquid used in the suspension may be deionized water when an additional conductive liquid is used therewith or when another flow of electrolyte solution is used with the flow of suspension to establish the spray of particles.

As known to one skilled in the art, various inert particles may be used as the carrier particles. For example, such inert carrier particles may include ferrite crystals, gold, tungsten spheres, and other metal spheres, as well as spheres and particles such as glass, polystyrene, and latex beads.

Preferably, the carrier particles are only mixed in the suspension with the biological material. However, such carrier particles may be coated or impregnated with biological material or otherwise associated therewith. For example, biological material may be coated on, bonded on, or precipitated onto the surface of the carrier particles or impregnated with the biological material. As described above, the carrier particles generally become associated with the biological material as the suspension is spray. The carrier particles act as the carrier for carrying the biological materials into the target cells. When one or more carrier particles having biological material associated therewith penetrate the cell membrane of the target cells, the biological material is dispersed within the cell.

Biological material which can be used with the inert carrier particles include but are not limited to biological stains such as fluorescent or radio-labeled probes, viruses, organelles, vesicles, peptides, ammoacids, lipids, proteins such as enzymes or hormones, nucleic acids, polynucleic acids including DNA and RNA, individual nucleic acids, small molecules such as bioactive substances, drugs, or the like. The biological material may be of a dry form or a wet solution. However, the present invention is clearly not limited to the materials listed herein.

Although it is preferred that a suspension of carrier particles and biological material or a suspension of biological material be used in accordance with the present invention, the present invention also contemplates other forms of biological material particles, i.e., in both dry form or suspended. For example, such biological material particles may include biological material which is freeze-dried or otherwise prepared as free particles or otherwise used as a particle for impact with target cells to penetrate such cells. Once the biological material particles have penetrated the target cells, such biological material particles or portions thereof would be expected to return to their natural state undamaged or otherwise contribute a desired biological activity within the target cell. For example, the biological material particles may return to their natural state by hydration, thawing, dissolving, etc.

The particle suspension from source 22 is provided to feeder 24 which controls the continuous flow of the source material to the electrospray dispensing device 12 when operable. The feeder 24 may be a liquid pump (e.g., a syringe pump, a gravity feed pump, a pressure regulated liquid reservoir, etc.), a mass flow controller, or any other flow control device suitable for feeding the source material to the dispensing device as would be known to one skilled in the art. The flow of a particle suspension, i.e., a solution, is atomized into microdroplets by the dispensing device 12. Atomization may be provided by any known technique for producing microdroplets, which microdroplets preferably have a nominal diameter of about 10 nm or greater, more preferably about 20 nm to about 10 $\mu$m, and even more preferably about 30 nm to about 1 $\mu$m. Preferably, electrostatic atomization is used. However, other atomization devices (e.g., pressure regulated atomizers, ultrasonic nebulizers, hydraulic nozzles, etc.) may provide adequate atomization. As described in the papers entitled, "Electrospraying of Conducting Liquids for Dispersed Aerosol Generation in the 4 nm to 1.8 $\mu$m Diameter Range," by Chen et al., *J. Aerosol Sci.*, Vol. 26, No. 6, pp. 963–977 (1995) and entitled "Experimental Investigation of Scaling Laws for Electrospraying: Dielectric Constant Effect," by Chen et al., *Aerosol Science and Technology*, 27:367–380 (1997) which are hereby incorporated in their entirety by reference, microdroplets having nominal diameters in the range of about 10 nm to about 2 micron can be produced by electrospray. Various factors as described in such references affect the produced droplet size. For example, capillary size, liquid feed rate to the dispensing device, surrounding gas properties, etc. One skilled in the art will recognize that such factors and others may be modified to produce microdroplets of desired sizes.

By applying different electrical potential differences between the capillary tube electrode 18 and the second electrode 21, different operating modes can be established. For example, a high positive voltage 20 is applied to capillary tube electrode 18 with the grounding of the electrode 21 to provide the spray 28 with a relatively high positive charge. For example, the high voltage source 20 may apply a high positive voltage preferably in the range of about 2000 volts to about 50,000 volts and more preferably 2000 volts to about 10,000 volts. The second electrode 21 in such a case may be provided to ground 38 or may have a negative voltage connected thereto. With relatively large potential differences being applied, as described in the above papers, pulsating modes or cone jet modes of operation are achieved. In a cone jet mode of operation, a cone shaped liquid meniscus is formed at the dispensing tip 23 whereas in the pulsating mode, the shape of the liquid meniscus alternates between a cone shape and a round shape. On the other hand, with relatively low electrical potential differences applied between the capillary tube electrode 18 and the second electrode 21, dripping from the dispensing tip occurs.

One skilled in the art will recognize that a high positive voltage may be applied to electrode 21 with the tube electrode 18 grounded to provide a highly negative charge on the particles of the spray 28. The only requirement necessary for the potential difference supplied between the capillary tube electrode 18 of the distributor head 19 and the second electrode 21 is that the electrical potential difference provides for a nonuniform electric field for establishment of a charged spray 28. The charge on the particles of the spray 28 must be concentrated such that the space charge effect of the charged particles allows forcible contact with the target cells 40, and preferably, allows for penetration of such target cells 40.

It is noted that the particle velocity is established primarily by the space charge effect due to the concentrated charge on the particles of the spray. Only secondarily is the velocity of the particles provided by the attractive forces between the charged spray 28 and the second electrode 21. It has been determined that for particles of relatively larger size, e.g., particles having nominal diameters less than about 0.5 microns, less than about 5 percent of the velocity is due to the electric field created by the applied voltage. Further, for particles of relatively smaller sizes, e.g. particles having nominal diameters of less than about 0.05 microns, less than 1 percent of the velocity is due to the electric field created by the applied voltage. Initially upon being dispensed from the dispensing tip 23, the charged particle velocity is due to the electric field created by the applied voltage. However, such initial velocity is almost immediately overtaken by the tremendous velocity attainable due to the space charge effect of the charged particles. The second electrode 21 is primarily used for establishment of the charged spray forward of the dispensing tip 23, and further is used for directing the particles of the spray and containment thereof.

Although various configurations for the dispensing device may be suitable, the dispensing device 12 preferably includes a capillary tube made of a suitable material, such as, for example, platinum, silica, etc. for providing the spray 28. For example, the capillary tube may have an outer diameter in the preferred range of about 6 $\mu$m to about 2.5 mm and an inner diameter in the preferred range of about 6 $\mu$m to about 2 mm. Further, the dispensing device 12 may include a conductive or nonconductive casing concentric to the capillary tube, which is used to provide a sheath of gas, e.g., $CO_2$, $SF_6$, etc., around the capillary tube to increase the electrostatic breakdown voltage for the capillary tube, e.g., to prevent corona discharge. The use of such a sheath of gas is particularly beneficial when the spray is created using a high surface tension liquid, e.g., deionized water. Several detailed configurations for the dispensing device 12 are described in further detail below.

The desired velocity to which the particles of the spray 28 are accelerated depends upon various factors. For example, such factors include but are clearly not limited to the charge on the particles, whether a vacuum chamber is used, the size and density of the particles as well as the type of target cells 40 to be impacted. Preferably, the desired velocity is the minimum velocity necessary such that the particles can penetrate the cell membrane of the target cells 40. The velocity necessary to penetrate such cells will be dependent upon the type of target cell which, for example, may include bacteria, single cell protozoa, plant pollen, plant protoplast, embryos, callus tissue, animal cells including animal progenitor cells (including, but not limited to pluripotent cells, stem cells, eggs, oocytes, embryotic cells), animal bone marrow cells and precursor cells, muscle or epidermal cells, epithelial cells, blood cells, isolated tissue explants, various other plant cells, or various other animal cells. The target cells may be part of a tissue, may be a monolayer of cells, a multilayer of cells, a suspension of cells, as well as being affixed to a surface or may take any other form as would be readily apparent to one skilled in the art.

With the preferred configurations as described herein, velocities in the range of about 30 m/sec to about 600 m/sec for particles having nominal diameters in the range of about 2 nm to about 1 $\mu$m are possible. The velocities on the higher end of the range are primarily due to small particle size, high particle charge, and/or reduced pressure. Further, particles can be generated utilizing such a configuration and delivered to the target surface at rates in the range of about $10^8$ particles per second to about $10^{11}$ particles per second continuously. The particle generation rate may be increased by using multiple capillary tube electrodes. The preferred velocity, nominally in the range of about 150 m/sec to about 300 m/sec, is sufficient to penetrate but not cause damage to most types of target cells.

The spray of particles 28 established by electrospray dispensing device 12 when source 22 is a suspension including carrier particles and biological material is generally formed as previously described herein by dispensing microdroplets having the carrier particles and biological material suspended thereby. Thereafter, the microdroplets evaporate concentrating the charge of the microdroplets on carrier particles and biological material which typically becomes associated therewith. Likewise, the spray of particles 28 established by electrospray dispensing device 12 when source 22 is a suspension including bulk biological material is generally formed as previously described herein by dispensing microdroplets having biological material suspended thereby. Thereafter, evaporation of the microdroplets concentrates the charge of the microdroplets on the biological material. By controlling various parameters of the electrospray apparatus, the amount of biological material delivered for impact with the target cells 40 can be controlled. Further, the velocity of such particles may also be enhanced.

Several characteristics that can be controlled include microdroplet size, the concentration of biological materials, and carrier particle size of the particles suspended in the spray 28. First, velocity of the particles may be enhanced by controlling particle size, i.e., carrier particle size. Smaller dimensional particles may enable such particles to have higher velocities due to space charge effect.

Further, by controlling the size of the sprayed microdroplets and the carrier particle size, the amount of biological material delivered can be controlled and higher velocities for the particles can be attained. First, the microdroplet nominal diameter can be controlled. For example, the microdroplet diameter may be controlled by controlling the capillary size, the liquid feed rate for suspensions, the electrical conductivity of the suspension, etc. The nominal diameter typically falls in the ranges as described previously herein.

With the use of carrier particles having smaller nominal diameters relative to the microdroplets, such as particles having a nominal diameter in the range of about 2 nm to about 1000 nm, or preferably in the range of about 10 nm to about 100 nm (or by increasing the size of the microdroplets relative to the particles), the amount of charge the carrier particles can carry is increased. In other words, by increasing the size differential between the microdroplets and the particles, upon evaporation the carrier particles (e.g., gold) can carry a charge much higher than the Raleigh limit for typical liquid suspensions. In this manner, the space charge effect provides for attainment of a higher velocity such that the particles can penetrate to different depths of the cell tissues. Further, by use of a vacuum chamber into which the particles are sprayed, increased velocities can be achieved.

Further, microdroplets having sizes slightly larger than carrier particles and/or biological material suspended thereby may be produced. This results in uniform size particles without agglomerates being formed. The effect of space charge repulsion of the unipolarly charged particles keep them separate and prevent particle agglomeration in the spray, as well as provide the particles with the velocity necessary for forcible contact with the target cells, preferably, for penetration of the target cells.

Further, by controlling the size of the microdroplet and the size of the carrier particles, one particle per microdroplet is attainable. With a controlled flow and known concentration of biological material utilized in association with the carrier particles, the amount of biological material in spray 28, or delivered to the spray area, can be controlled and is reproducible, i.e., can be consistently repeated.

After the microdroplets of liquid suspending the particles and/or biological material, is dispensed, the solvent of the microdroplets begins to evaporate decreasing the size of the microdroplet. At the target cells 40, typically only the carrier particle having associated biological material (or biological material alone in the case of a biological material suspension without carrier particles) remains for impact with the target cells 40. The spray particle size can be made very small, as small as a few nanometers in diameter and still attain the necessary velocity under the effects of space charge. This makes it possible to deliver biological materials into smaller cells and tissues.

In addition to penetration of the cells as a result of the bombardment of the cells with material using the present invention, the electrospraying technique described herein may be used to produce liposome droplets encapsulating biological material, e.g., DNA. The liposome droplets can be directed by the electric field and distributed uniformly over target cells in manners similar to those described herein, e.g., movement of the target surface, movement of the distributor head, etc. As opposed to the penetration of the cells at impact, the liposomes encapsulating the biological material facilitate transfer of the material into the cells through fusion of the liposome with the cell membrane as is known to those skilled in the art. The liposome droplets may be of varying sizes, e.g., a nominal diameter of about 10 nm to about 10 µm. The electrospraying technique used to direct the liposomes onto the cells can be adjusted (e.g., distance of nozzle to target surface can be adjusted, electrical potential or strength of the field can be adjusted, etc.) to vary the velocity of the liposome droplets such that the liposome droplets land appropriately for the fusion mechanism to be accomplished.

Figure 2:
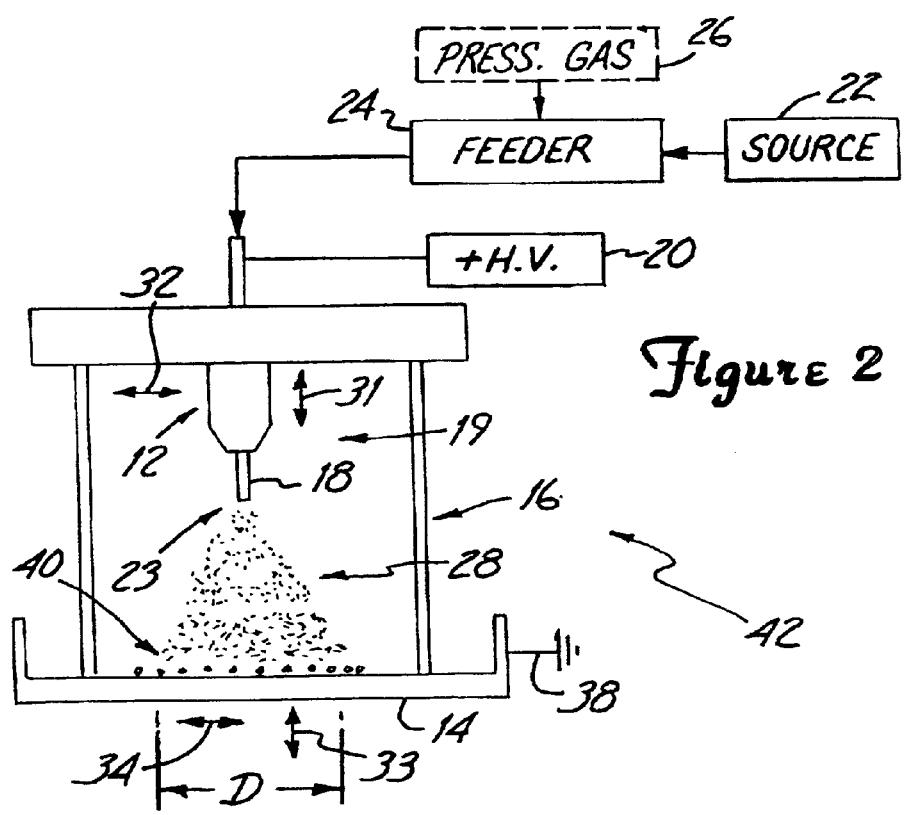
FIG. 2 is a diagrammatical illustration of another embodiment of an electrospraying apparatus of FIG. 1B in accordance with the present invention.

One embodiment of an electrospraying apparatus 42 in accordance with the present invention is shown in FIG. 2. Generally, the electrospray dispensing device 12 positioned for providing a spray 28 into a chamber 16 is substantially equivalent to that described generally with respect to FIG. 1C as indicated by like reference numbers being used for like elements. However, in the embodiment of FIG. 2, a target surface 14 having one or more target cells 40 placed thereon is positioned downstream from or forward of the dispensing device 12.

The spray 28 has a first electrical charge concentrated on the particles as previously described herein upon evaporation of the microdroplets in the electric field created by the high voltage source 20 applied to the capillary tube electrode 18 and the grounding of target surface 14. The capillary tube electrode 18 functions as the first electrode as described with reference to FIG. 1B and the conductive target surface 14 functions as the second electrode described with reference to FIG. 1B. With an electrical potential difference established between the capillary tube electrode 18 and target surface 14, a nonuniform electric field is provided from the dispensing tip 23 to the target surface 14 to establish the spray of particles 28 forward of the dispensing tip 23. In addition to creating the nonuniform electric field for establishing the spray of particles 28, the conductive target surface 14 connected to ground 38 also provides for containment of the particles to a certain area to allow for forcible contact with the target cells 40.

As shown in FIG. 2, depending on the dispensing device used and other components of the apparatus, the particle suspension provided from source 22 may be from a pressurized source. Alternatively, a pressurized gas source 26 may be utilized in conjunction with feeder 24 or another portion of the dispensing device 12 so as to provide pressure to dispense the spray 28 into chamber 16. For example, the source 22 may be pressurized in the range of a few tenths of an atmosphere to a few 100 atmospheres, or the pressurized gas source 26 utilized may be a gas such as, for example, carbon dioxide, ambient air, hydrogen, helium, nitrogen, and be at similar pressures.

The target surface 14 may be any suitable surface for placement of target cells. For example, the target surface may be an electrically conducting surface connected to an electrical ground or charge. Generally, the cells may be made conductive to the target surface by the natural moistness of the cells or made conductive by any other manner, e.g., coating, nutriant solutions. The target surface 14 is a substantially horizontal surface capable of supporting the target cells thereon. The electrical potential or ground may be applied to the target surface such that a portion or the entire surface attracts the spray, e.g., the particles are directed to particular areas of the target surface by the electrical field set up by the potential difference applied between the distributor head and the target surface. Being able to direct the spray to a particular portion of the target surface is beneficial in that overspray is avoided. In other words, the spray is attracted to a portion of the target surface having a voltage applied thereto, e.g., a portion insulated from the other portions, where target cells have been positioned. It is even possible to adjust the electrical field between the distributor head 19 and the target surface 14 such that the particles are directed from one position of the target surface to another, such as by switching mechanisms or alternative voltage sources applied thereto.

Preferably, the target surface 14 is moveable along the x, y, z axes as indicated generally with arrows 33 and 34. The target surface 14 is provided with, and supported by, a movable positioning member (not shown) which enables it to move the target surface along such axes. For example, the target surface may be moved either closer to or farther away from the electrospray dispensing device 12. The distance between the dispensing tip 23 of the distributor head 19 in the chamber 16 and the target surface 14 is preferably in the range of about 5 mm to about 3 cm depending on the desired electric field and spray area (D) desired. However, this distance may vary depending on the specific application, and it is apparent that the spray area D will have a lesser diameter as the dispensing tip 23 of the distributor head 19 and target surface 14 are moved closer to one another.

Since all the particles of the spray 28 carry the same polarity charge as they are dispensed into the chamber 16, the particles tend to repel each other and avoid agglomeration. The electrospray technique can cover the spray area D uniformly. It should be noted that the repulsion of the same polarity charged particles will, at least in part, determine the spread of the spray 28 dispensed in the chamber 16.

Figure 3:
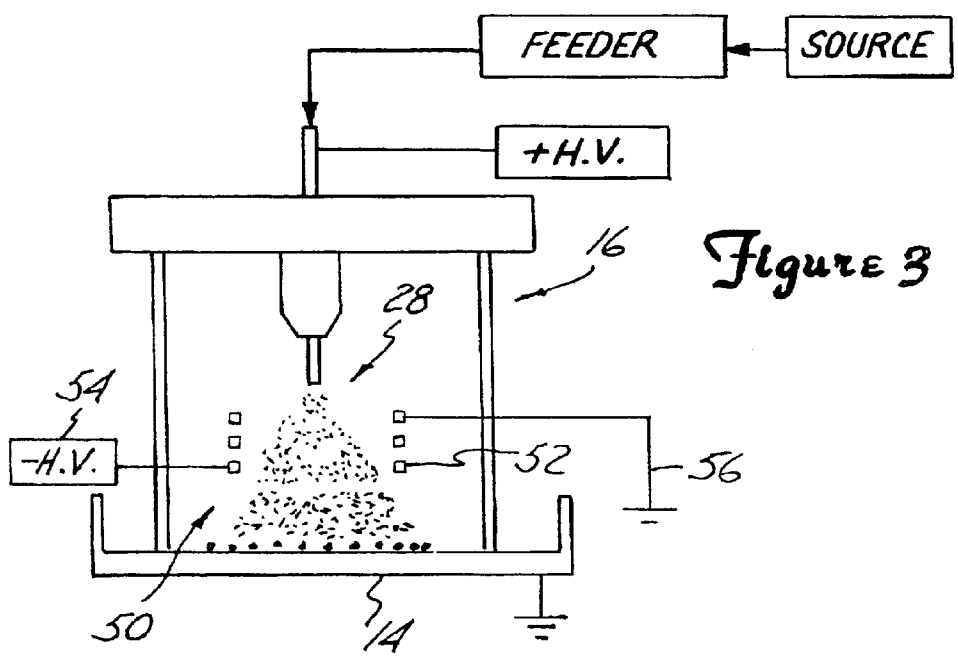
FIG. 3 is a diagrammatical illustration of the apparatus shown in FIG. 2 including an additional electrostatic acceleration field.
Figure 4:
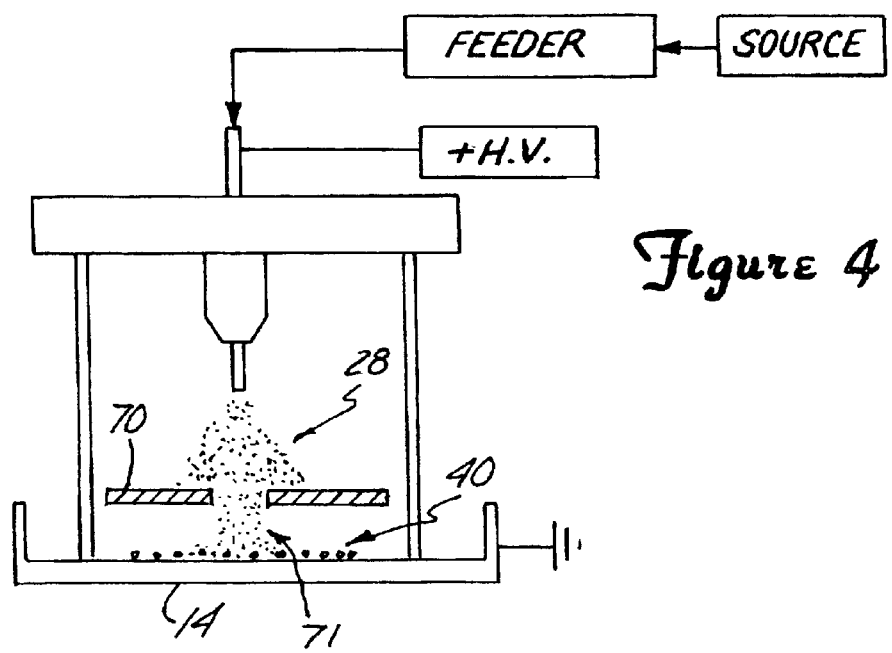
FIG. 4 is a diagrammatical illustration of the apparatus of FIG. 2 including a placement control member.
Figure 5:
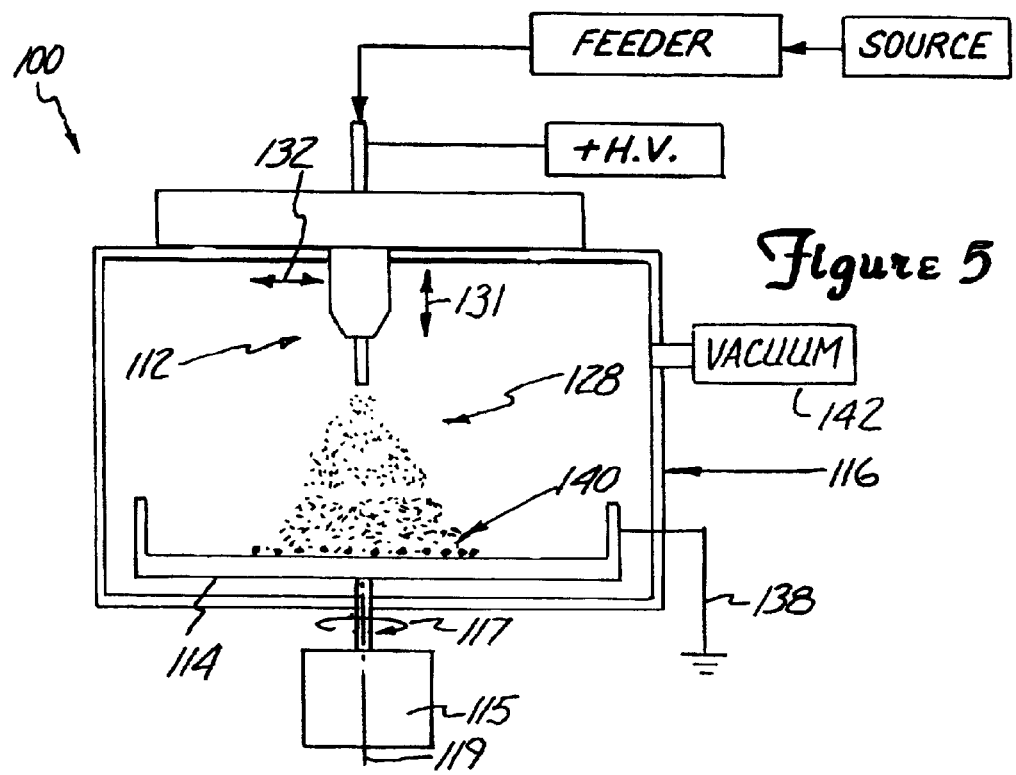
FIG. 5 is a diagrammatical illustration of an alternate electrospraying apparatus in accordance with the present invention using a vacuum chamber.
Figure 6:
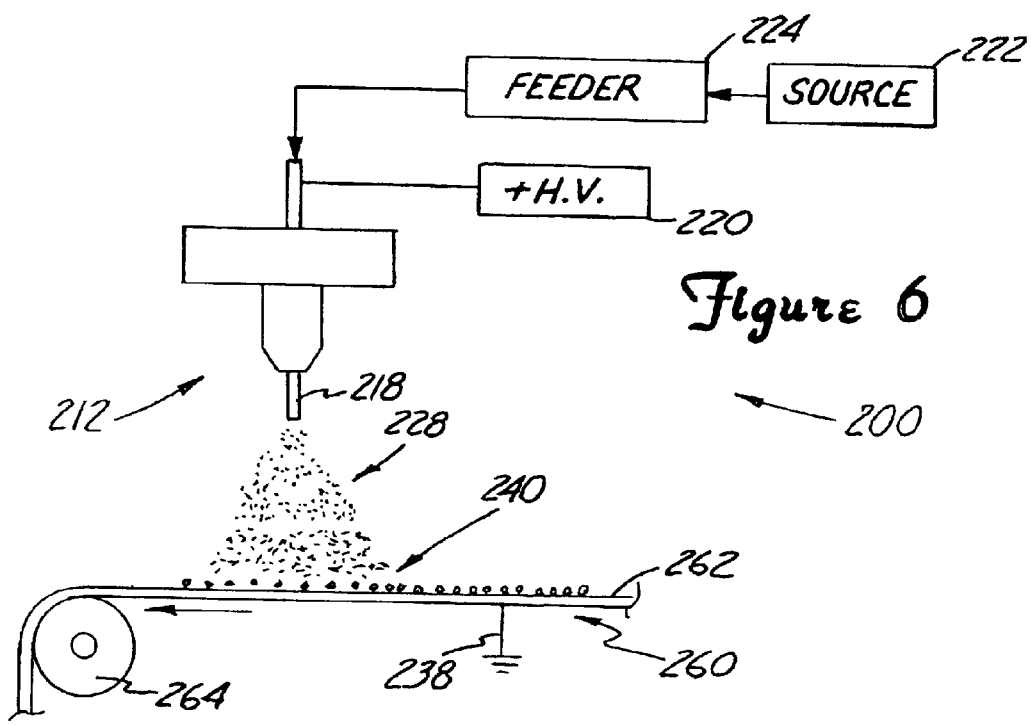
FIG. 6 is a further alternate electrospraying apparatus in accordance with the present invention illustrating a continuous electrospraying apparatus.

FIG. 3 diagrammatically shows the electrospraying apparatus 42 of FIG. 2 with the addition of an external electrostatic field 50 for further accelerating the charged particles of spray 28 dispensed into chamber 16. The external electrostatic field 50 is provided using ring electrodes 52 having a negative high voltage supply 54 connected thereto and further connected to ground 56. The field accelerates the charged particles dispensed into the chamber 16 through the ring electrodes. In such a manner, the particles are further accelerated towards grounded target surface 14. The voltages applied to the ring electrodes may be in the preferable range of about 200 V to about 5 kV.

Figure 7:
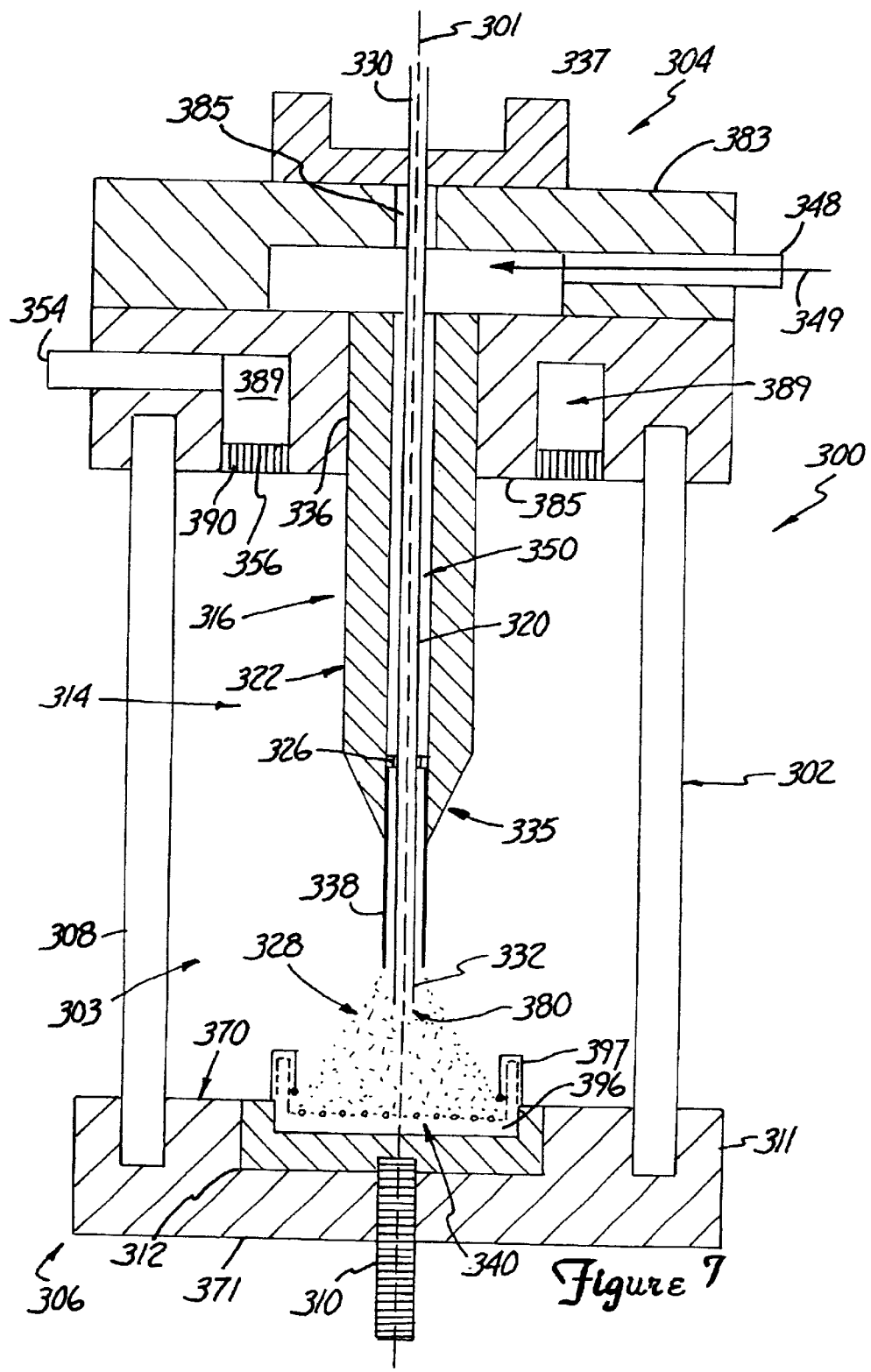
FIG. 7 is a more detailed diagram of a portion of the electrospraying apparatus in accordance with the present invention having a single capillary tube distributor head.
Figure 8:
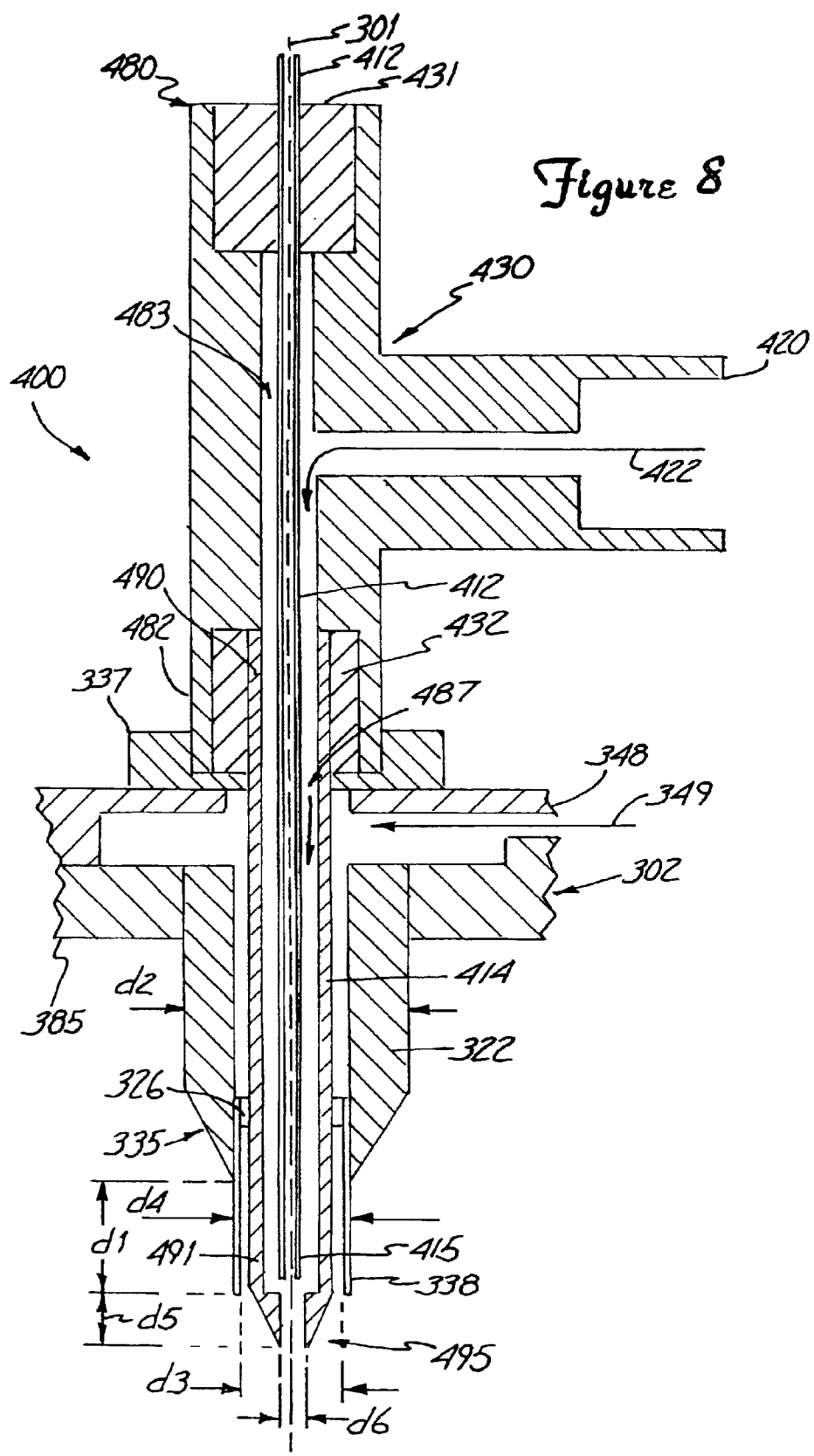
FIG. 8 is a more detailed diagram of an alternate capillary configuration for use in the apparatus shown in FIG. 7 including a dual capillary tube distributor head.

It should be readily apparent to one skilled in the art that the acceleration of the charged particles of the spray 28 by the external electric field 50 may be needed for accelerating the particles to a desired velocity necessary for penetrating certain target cells 40 on target surface 14. However, in accordance with the present invention, such added acceleration is generally unnecessary as the space charge effect provides the necessary velocity for such penetration.

FIG. 4 diagrammatically illustrates the electrospraying apparatus 42 as shown in FIG. 2 but further includes a placement control member 70. Placement control member 70 includes an opening 71 which allows a portion of the particles of spray 28 therethrough for impact with target cells 40. In such a manner, the particular target cells 40 to be impacted can be controlled.

FIG. 5 is a diagrammatical illustration of an alternative electrospraying apparatus 100 which is similar to the electrospraying apparatus 42 of FIG. 2 but which includes several additional beneficial components. The electrospraying apparatus 100 includes electrospray dispensing device 112 substantially identical to that shown in FIG. 1 but which dispenses the spray 128 into a vacuum chamber 116 evacuated by vacuum pump 142. The velocity of the particles of spray 128 due to the space charge effect is generally greater as the pressure in chamber 116 is decreased. Preferably, the pressure in the chamber is in the range of about 1 atmosphere to about 0.1 atmosphere.

The electrospray apparatus 100 further includes a target surface 114 whereon target cells 140 are placed and which is connected to ground 138. The target surface is rotatable around axis 119 utilizing a motorized positioning member 115. The target surface 114 can then be rotated and a more uniform distribution of the particles of spray 128 is delivered to the target cells 140. Further, the dispensing device 112 is movable along the x, y, z axis as represented generally by arrows 131 and 132. As such, particles can be delivered for impact with the entire area of the rotating surface 114. For example, the dispensing device 112 can be positioned away from the axis 119 (e.g., half the distance between axis 119 and the edge of the rotatable target surface 114). In this manner, the spray 128 can be uniformly distributed on the cells on the target surface 114 as the target surface rotates.

FIG. 6 diagrammatically illustrates an alternative electrospraying apparatus configuration 200. The electrospraying apparatus 200 includes a conveyer system 260 which is positioned relative to dispensing device 212. Dispensing device 212 is like an electrospray dispensing device described herein. The electrical potential difference for providing the spray from the dispensing device 212 is applied using voltage source 220 and grounding the conveyor system 260. The conveyer system 260 includes target surface 262 which is moved by motorized element 264. In such a manner, the continuous providing of spray 228 with the continuous movement of target surface 262 having target cells 240 placed thereon provides for a mass production system for transfer of biological material to target cells.

It will be readily apparent that the cells to be modified by the biological material may be in their natural state, e.g., in situ. Such cells may be treated while in the body of an animal, i.e., in vivo, or when such cells are removed from the body, i.e., ex vivo. For example, tissues which can be bombarded include human tissue or other animal tissues such as epidermal tissue, organ tissue, tumor tissue, plant tissue and like, while in the body or removed from the body. A portable electrospraying apparatus for gene therapy or other specialized in situ applications, e.g., immunization, may be used. For example, in such a portable configuration, the target cells to be impacted by the charged particles may be situ cells, as opposed to the cells being on a target surface. An illustrative portable electrospraying apparatus is generally described below with reference to FIG. 9 and will generally include elements or components similar in function to the configuration of FIG. 1C.

It should be apparent to one skilled in the art that the various elements described in reference to FIGS. 1–6 may be combined in a variety of manners and each alternative configuration of the electrospraying apparatus described herein is for illustration purposes only. For example, the vacuum chamber 116 described with reference to FIG. 5 may be utilized with the electrospray apparatus of FIG. 4, the placement member 70 described with reference to FIG. 4 may be utilized in the electrospray apparatus 42 of FIG. 2, the conveyer system 260 as described with reference to FIG. 6 may be utilized with the external electric field 50 as described with reference to FIG. 3, etc.

FIG. 7 is a more detailed diagram of one configuration of a portion 300 of the electrospraying apparatus shown generally in FIG. 2 including a dispensing device 314 according to the present invention. As shown in FIG. 7, spray 328 is sprayed into a chamber 303 defined by a housing 302 having an axis 301 therethrough. The housing 302 includes a first end 304 and a second end 306 connected therebetween with a cylindrical wall about axis 301. Preferably, the housing 302 is a vacuum chamber which can be evacuated as described further below. It will be recognized that various configurations may be selected for creating the housing 302 and that the present invention is not limited to any particular configurations. The housing 302 is generally formed of insulative materials. For example, the cylindrical wall enclosure 308 is preferably a plexiglass cylindrical wall for visibility while the first and second ends 304, 306 may be formed of various insulative materials. First end 304 may also be formed of conductive portions to facilitate application of voltages or ground to the capillary tube 320.

The second end 306 of the housing 302 includes an end element 311 connected to the cylindrical walls 308. Positioned relative to an upper surface 370 of the end element 311 is a target platform 312 upon which target cells can be positioned. For example, a tube, dish, or any other structure may be positioned on the platform 312 which includes cells or the cells may be positioned on the platform 312 without any additional structure. Further, a rotatable micrometer adjustment mechanism 310 is provided through a lower surface 371 of the end element 311 for contact with platform 312 such that the height of the platform 312 can be varied, e.g., the distance between the target cells 340 and the dispensing tip 380 of the dispensing device 314 can be adjusted. The platform 312 is formed of a conductive material, e.g., stainless steel, and may function as the second electrode of the dispensing device 314 for establishing spray 328 from the dispensing tip 380 of the dispensing device 314.

The first end 304 of the housing 302 includes a distributor head 316 extending therethrough having an axis that is coincident with axis 301 for use in establishing the spray 328 in the chamber 303 in combination with conductive platform 312. The distributor head 316 includes a capillary tube 320 having an axis therethrough coincident with axis 301. The capillary tube 320 includes a first end 330 sealingly positioned in aperture 385 of the first end 330 by conductive sealing element 337 at the upper surface 383 of the first end 304. The capillary tube 320 further includes a second end 332 positioned for dispensing spray 328 as desired. The capillary tube 320 may be made of any suitable material, such as, for example, platinum, silica, stainless steel, etc. and may be of any suitable size. For example, the capillary tube may preferably have an outer diameter in the range of about 8 $\mu$m to about 2.5 mm, and an inner diameter in the preferred range of about 6 $\mu$m to about 2 mm. More preferably, the inner diameter of the capillary tube is in the range of about 10 $\mu$m to about 200 $\mu$m.

Further, the distributor head 316 includes a nozzle portion or casing 322 which as illustrated in FIG. 7 is an elongate substantially cylindrical metal casing concentric with the capillary tube 320. However, the casing 322 can be conductive or nonconductive. Further, the casing 322 can take any configuration or shape which allows for the flow of a sheath gas about the capillary tube 320. Together, in this particular embodiment, the capillary tube 320 and the casing 322 form the capillary tube electrode of the distributor head 316 for use in providing the spray 328 into the chamber in conjunction with the conductive platform 312. The casing or nozzle portion 322 includes a first end portion 336 which tapers at section 335 thereof to a narrower second end portion 338. The second end portion 338 extends from the tapered section 335 and is concentric with the second end 332 of the capillary tube 320. The narrow end of the tapered section 335 extends a preferable distance of about 5 mm to about 5 cm from the lower surface 385 of the first end 304. The outer diameter of the second end portion 338 is preferably in the range of about 2 mm to about 5 mm and the inner diameter of the second end portion 338 is preferably in the range of about 0.1 cm to about 0.2 cm. The second end 332 of the capillary tube 320 extends beyond the second end portion of the metal casing or nozzle portion 322 towards the target cells 340 by a distance of preferably about 2 mm to about 5 mm. The nozzle portion 322 is formed of any suitable metal or nonconductive material such as stainless steel, brass, alumina, or any other suitable conductive or nonconductive material. The nozzle portion 322 is spaced from the capillary tube 320 by spacers 326 or other spacing structures. For example, a metal casing 322 may be deformed at particular portions, such as pin points or depressions, to create a neck for centering the capillary tube 320 therein.

The capillary tube electrode may take one of many configurations. However, of primary importance is that the capillary tube electrode provide an electrode for creating the nonuniform electric field and provide at least a gas sheath about the capillary tube to avoid corona discharge if spraying high surface tension liquids, e.g., deionized water. For example, in an electrospraying apparatus wherein the spray is established in a chamber, the capillary tube electrode may just include a capillary tube itself, as opposed to requiring a casing such as metal casing 322 to provide an annular space for flow of the sheath gas. In such a configuration, the chamber may be flooded with the gas for preventing corona discharge. Further, when spraying liquids other than high surface tension liquids, the gas sheath may not be required.

A gas inlet 348 is provided in the first end 304 of housing 302 to allow for input of a stream of electro-negative gases, e.g., $CO_2$, $SF_6$, etc., to form a gas sheath about the capillary tube 320. The inlet is configured for directing a stream of an electro-negative gas in an aperture 350 between the concentric capillary tube 320 and the nozzle portion 322. This gas sheath allows the applied voltage to be raised to higher levels without corona discharge, e.g., the electrostatic breakdown voltage for the capillary tube electrode is increased. The entire portion of end 304 or portions thereof may be formed of conductive materials to facilitate application of a voltage or ground to the capillary tube electrode. For example, sealing elements 337 may be nonconductive, but is preferably conductive to facilitate application of a voltage or ground to capillary tube 320.

The first end 304 further includes an exit port 354 for gases to exit the chamber 303. For example, the exit port 354 may open into an annular chamber 389 defined in the first end 304 having a bottom face plate 390 having a series of holes for allowing flow from the chamber 303 out through the exit port 354. A vacuum pump may be connected to the exit port 354 for evacuating the chamber 303 to a low pressure. For example, preferably, the pressure in the chamber is in the range of about 1 atmosphere to about 0.1 atmosphere. Further, instead of or in addition to providing the gas sheath between the capillary tube 320 and the nozzle portion 322, the chamber 303 may be flooded with a gas through the exit port 354 to increase the electrostatic breakdown voltage for the capillary tube electrode.

In one embodiment, the chamber 303 is flooded with the gas through the exit port 354 and then a flow in the preferred range of about 5 cc/min to about 200 cc/min is continued through the exit port 354. Any port to the chamber 303 may be used for exit of gas from the flooded chamber, e.g., such as a port that is available for sensing pressure (not shown) in the chamber. When the chamber 303 is flooded, the gas sheath between the capillary tube 320 and the nozzle portion 322 may not be necessary. As such, flooding of the chamber is an alternative to the use of such a gas sheath between the capillary tube 320 and the nozzle portion 322.

To establish the spray 328 in the chamber 303, biological material is provided, e.g., suspended in a solution, and received in the first end 330 of the capillary tube 320. Preferably, the flow rate of the suspension may be in the range of about 0.01 $\mu$l/min to about 5 $\mu$l/min. Preferably, a relatively high voltage, for example, in the range of about 2000 volts to about 6000 volts, may be applied to the platform 312 relative to the capillary tube 320 which is electrically grounded (or vice versa) to establish the potential difference between the first and second electrode of the spraying apparatus. In this particular illustrative configuration, capillary tube 320, metal casing 322, and sealing element 337 are conductive. Spray 328 is established forward of the dispensing tip 380 of the second end 332 of the capillary tube 320 per a mode of operation as previously described. The potential difference between the electrodes establishes an electric field therebetween causing the formation of a smaller filament at the meniscus formed at the dispensing tip 380 while attracting the suspension downward toward the target cells.

FIG. 8 is a more detailed diagram of an alternate capillary electrode configuration 400 for the distributor head 316 of FIG. 7. Like reference numbers are used in FIG. 8 for corresponding like elements of FIG. 7 to simplify description of the alternate capillary configuration 400. Generally, the alternate capillary electrode configuration 400 is substituted for or replaces the single capillary tube 320 of the structure shown in FIG. 7.

The capillary electrode configuration 400 includes a first capillary tube 412 having an axis coincident with axis 301 for receiving biological material from a source, e.g., a suspension of biological material. Further, a second capillary tube 414 is concentric with the first capillary tube 412. An annular space 487 between the inner and outer capillaries 412, 414 is used to direct a stream of electrolyte liquids of controlled conductivities to the dispensing tip 495 for use in establishing the spray forward thereof. The use of an electrolyte solution flowing to the dispensing tip 495 for establishing the spray of microdroplets therefrom, allows the suspension of biological material to be prepared with deionized water which has characteristics, e.g., pH, that do not disturb the biological material properties. With use of the electrolyte solution, sufficient charge is achieved on the microdroplets which thereafter concentrates on the particles of the spray to allow space charge effects of the particles to attain sufficient velocities for penetrating target cells. Without the second flow of electrolyte solution, an electrolyte solution may need to be added to the suspension to achieve such charge concentration. Further, the electrolyte solution characteristics, e.g., conductivity, can be changed to adjust the charge concentrated on the particles without the need to change the suspension characteristics. The stream of electrolyte liquids is directed in the annular space 487 such that it comes into contact with the suspension proximate the dispensing tip 495.

In more detail, the housing portion 430 includes an aperture 483 extending from a first end 480 of the housing portion 430 to a second end 482 thereof. An inlet port 420 opens into the aperture 483. The inlet port 420 receives a flow of electrolyte liquids 422 to be directed in the annular space 487 about the capillary tube 412. The first capillary tube 412 has a first end 413 and a second end 415. The capillary tube 412 is positioned in the aperture 483 of the housing portion 430 of generally T-shaped configuration. The first end 413 of the capillary tube 412 is sealed to housing 430 using conductive element 431 at the first end 480 of the housing portion 430. The capillary tube 412 extends from the second end 482 of the housing portion 430 and with the second capillary tube 414 forms the annular space The second capillary tube 414 includes a first end 490 and a second end 491. The second capillary tube 414 is positioned so that it is concentric with the first capillary tube 412. The first end 490 of the second capillary tube 412 is coupled to the second end 482 of the housing portion 430 using conductive element 432. Further, the second end 491 of the second capillary tube 414 is held in place relative to the nozzle portion 322 by spacers 326. The second capillary tube 414 extends beyond the first capillary tube 412 a predetermined distance in the direction of the target cells of preferably about 0.2 mm to about 1 mm. The portion of the second capillary tube 414 at the dispensing tip 495 which extends beyond the first capillary tube is tapered at a 60 degree to 75 degree angle for obtaining stable spray pattern and operation mode, i.e., consistent spraying patterns. Without the taper, intermittent operation may occur. Further, the second capillary tube 414 extends beyond the second end 338 of the nozzle portion 322 a predetermined distance (d5), preferably about 2 mm to about 5 mm. The first capillary tube 412 has preferable diameters like that of capillary tube 320 of FIG. 7. The second capillary tube concentric with the first capillary tube has a preferable outer diameter of about 533.4 $\mu$m to about 546.1 $\mu$m and a preferable inner diameter of about 393.7 $\mu$m to about 431.8 $\mu$m. The gap d6 at the tip of the second capillary tube 414 is preferably in the range of about 10 $\mu$m to about 80 $\mu$m. The other preferred configuration parameters are substantially equivalent to that described with reference to FIG. 7.

In such a configuration, dual streams of liquids are provided for establishing a spray from dispensing tip 495 of the apparatus when a suspension of biological material or a suspension of carrier particles and biological material are used. This provides the benefits as previously described. Further, a gas sheath may also be provided through inlet port 348 as previously described with reference to FIG. 7. Yet further, the first capillary tube 412 may extend beyond the end of the second capillary tube 414, e.g., the dispensing tip is formed at the end of first capillary tube 412 which is closer to the target cells than the end of the second capillary tube 414. In other words, the suspension may contact the electrolyte solution before exiting the dispensing tip 495 or the suspension may contact the electrolyte solution upon exiting the end of the first capillary tube 412. Further, the second capillary tube may take various other configurations to form the space for providing the electrolyte solution to the dispensing tip, e.g., not necessarily a capillary tube structure.

The first or center capillary may be used to spray suspensions of biological material with or without the use of carrier particles. The rate of flow of such suspensions may vary. Preferably, the flow rate is about 0.01 $\mu$l/min to about 2.0 $\mu$l/min. The annular space between the inner 412 and outer 414 capillaries is used to direct the stream of electrolyte liquids of controlled conductivities. The rate of flow of such electrolyte liquids may vary. Preferably, the flow rate is about 0.1 to about 5 $\mu$l/min. For example, such electrolyte solutions may include deionized water with a trace of nitric acid, nutrient liquids used for growing cultured cells, or any other suitable component for biological material suspensions or target cells. The electrical conductivity of such electrolyte liquids is preferably in the range of about 60 $\mu\Omega^{-1}$/cm to about 80,000 $\mu\Omega^{-1}$/cm.

In addition to controlling conductivity and therefore the charge of the particles sprayed, the dual stream of liquids can further be used for other purposes. For example, the outer stream may be a suspension of liposomes that are sprayed with a suspension of other biological, e.g., DNA, provided through the center capillary. As such, the outer flow of the suspension includes an agent, e.g., liposomes, which is used to promote penetration of the target cells, e.g., dissolve the outer linings.

Figure 9:
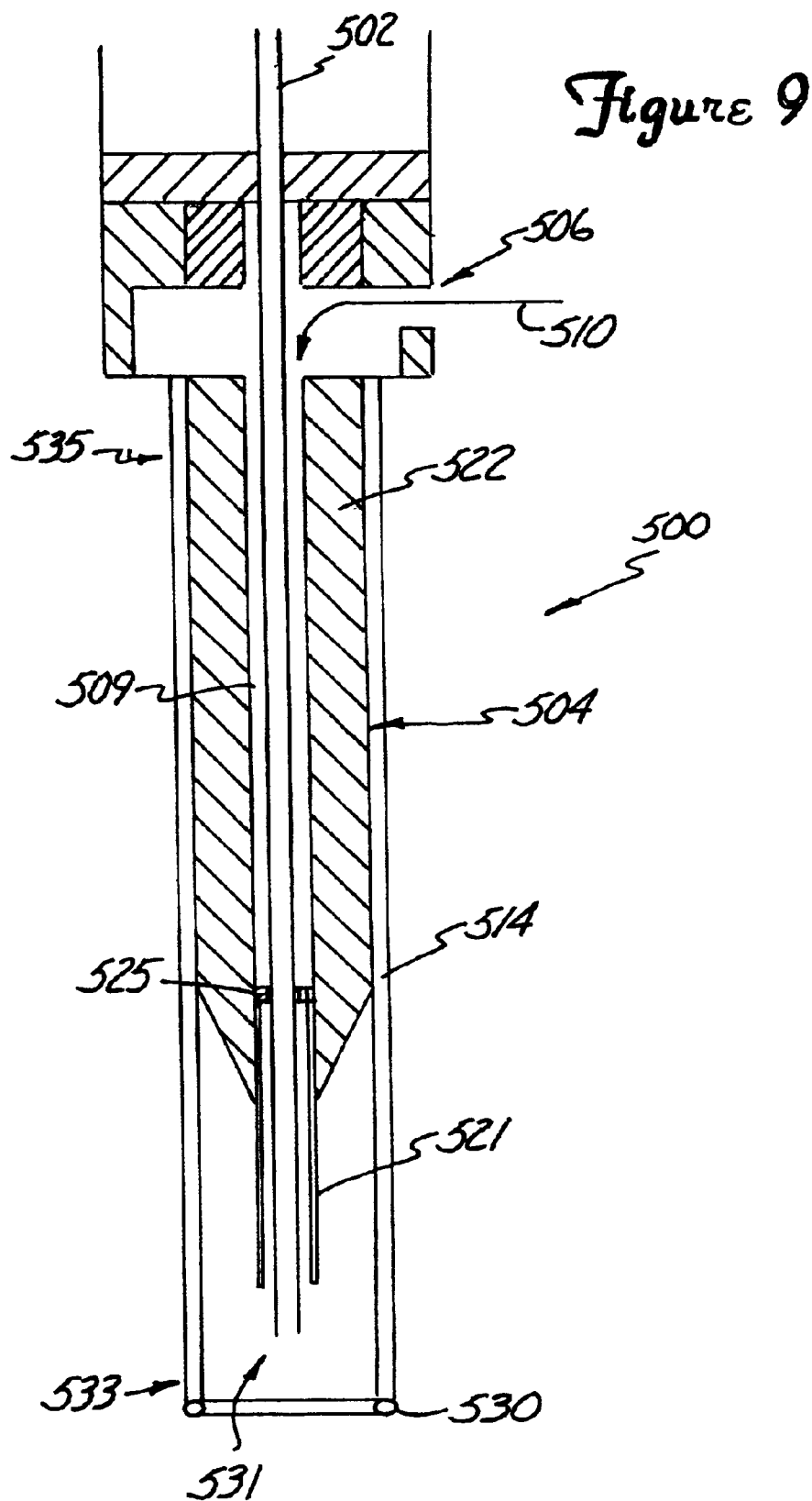
FIG. 9 shows an illustrative diagram of a portion of a compact pen-like electrospraying apparatus in accordance with the present invention.

FIG. 9 shows an illustrative diagram of a dispensing device 500 for a compact pen-like electrospraying apparatus in accordance with the present invention that may be used for introduction of biological material into cells, such as in situ cells, e.g., human tissue or other animal tissues such as epidermal tissue, organ tissue, tumor tissue, plant tissue and the like. The dispensing device 500 includes a capillary tube 502 and a nozzle portion 504 configured substantially the same as described with reference to FIG. 7. The apparatus further includes a gas sheath 509 provided between the capillary tube 502 and the nozzle portion 504. The main difference between the apparatus as shown in FIG. 7 and that of FIG. 9 is that a ring electrode 530 used for establishing the spray at the dispensing tip 531 is positioned at the second end 533 of a cylindrical insulative jacket 514 concentric with and preferably in contact with the nozzle portion 504 along at least a portion of a first end 535 of the jacket 514. With use of such a configuration, a chamber is eliminated.

EXAMPLE 1

Using an apparatus equivalent to that shown in and described with reference to FIG. 7 modified with the dual capillary tube distributor head 400 shown in and described with reference to FIG. 8, biological material transfer was successfully accomplished. The apparatus used was configured with a center capillary tube 413 having an outer diameter of about 229 $\mu$m to about 241 $\mu$m and an inner diameter of about 89 $\mu$m to about 127 $\mu$m. The second capillary tube 414 concentric with the center capillary tube had an outer diameter of about 533 $\mu$m to about 546 $\mu$m and an inner diameter of about 394 $\mu$m to about 432 $\mu$m. The distance d1 shown in FIG. 8 from the end of tapered section 335 to the end of the metal casing 322 is about 2 cm. The diameter d2 of the first end 336 of the nozzle portion or metal casing 322 is about 0.5 cm. The outer diameter d4 of the second end 338 of the nozzle portion 322 is about 1715 $\mu$m to about 1740 $\mu$m and an inner diameter d3 of about 1333 $\mu$m to about 1410 $\mu$m. The distance d5 from the tip of the second end 338 of the nozzle portion 322 to the tip of the end of the second capillary tube 414 is about 5 mm. The gap d6 at the tip of the second capillary tube 414 is about 40 $\mu$m.

The dispensing device was constructed of various materials. Primarily, the conductive elements were constructed of stainless steel, the chamber wall was made of plexiglass, and the insulative parts such as portions of the ends 304 and 306 were made of a plastic, black delrin, material.

The biological material source was a suspension of plasmid and Au particles having 5 and 10 nanometer diameters (available from Sigma of St. Louis, Mo.). The plasmid was a commercially available plasmid including EGFP gene (Enhanced Greeen Fluorescent Protein from a Jelly Fish). The plasmid is available under the designation EGFP from Clontech of Palo Alto, Calif. The plasmid was resuspended for use at 0.05 $\mu$grams/$\mu$liter in deionized water with a concentration of 0.01 percent Au particles.

The target cells were African Green Monkey fibroblast cells (COS-1) available from the American Type Culture Collection (Rockville, Md.) under the designation ATCC CRL-1650, Simian fibroblast like cells from kidney transformed with SV40 virus. The target cells were a monolayer at an estimated concentration of about 800 cells/$cm^2$. The target cells are in a Dulbecco's Modified Eagle Medium (DMEM-Hi) which includes 10 percent Fetal Calf Serum and 90 percent deionized water (available from Gibco/BRL of Rockville, Md.).

The electrospray was operated in a pulsating mode in a flooded chamber 302. The chamber 302 was flooded using a 50 cc/min flow of $CO_2$ through port 354. No gas sheath was provided about the second capillary tube 414. A voltage of 4300 volts was applied to conductive element 312 as shown in FIG. 7. The distance from the dispensing tip 495 of the second capillary tube 414 to the target cells 340 was about 2.5 cm. The cells were provided in a small well 396 (cut from a 12-well culture dish available from Corning of Cambridge, Mass.) formed of optically clear virgin polystyrene treated with optimal cell attachment and having a diameter of about 22 mm. The well 396 was placed on the platform 312 of the second end 306 of the housing 302. Conductive wires 397 were provided from inside the well 396 to the conductive platform 312 to bleed off stray charge and to form the spray as well.

The sheath liquid provided in the annular space 487 between the first and second capillary tubes 412, 414 was a 1 $\mu$l/min flow of deionized water plus a trace amount of nitric acid of a ratio of about (1:50) with an electrical conductivity of about 300 $\mu\Omega^{-1}$/cm. The suspension described above was provided by a syringe pump available under the designation of Harvard "33" Double syringe pump from Harvard Apparatus of Holliston, Mass. at a rate of 1.0 $\mu$l/min.

The cells were sprayed for about 2 minutes at a temperature of 20° C. and a pressure of 1 atmosphere. The well containing the target cells was placed in an incubator (available from NAPCO of Landrum, S.C.) for 1.5 days at a temperature of about 37° C., i.e., the time for cells to divide themselves and express fluorescence. A UV microscope available under the designation of Nikon Inverted Fluorescent Microscope from Fryer Co. of Minneapolis, Minn. was used to visually note the fluorescence. Approximately 40 percent to 60 percent of the cells fluoresced. As fluorescence was noted, introduction of biological material into the cell was successful.

EXAMPLE 2

The same setup of Example 1 was used. The only difference was that Au particles were not added to the suspension and the voltage applied to the element 312 was 5600 volts such that the dispensing device was operated in cone jet mode. Again, the UV microscope was used to visually note the fluorescence. Approximately 40 percent to 60 percent of the cells fluoresced. As fluorescence was noted, introduction of biological material into the cell was successful.

All patents and references disclosed herein are incorporated by reference in their entirety, as if individually incorporated. Further, although the present invention has been described with particular reference to various embodiments thereof, variations and modifications of the present invention can be made within the contemplated scope of the following claims as is readily known to one skilled in the art.

What is claimed is:

1. A method of coating particles, the method comprising:
providing at least one opening at a spray dispenser end;
providing a flow comprising at least one liquid suspension through the at least one opening, wherein the flow comprising the at least one liquid suspension comprises at least particles and a coating material;
establishing from at least the one liquid suspension a spray of microdroplets suspending at least the particles forward of the spray dispenser end by creating a nonuniform electrical field between the spray dispenser end and an electrode electrically isolated therefrom, wherein the particles are coated with at least a portion of the coating material as the microdroplet evaporates.

2. The method of claim 1, wherein the particles comprise carrier particles and the coating material comprises biological material.

3. The method of claim 1, wherein the at least one suspension comprises biological material particles.

4. The method of claim 3, wherein the coating material comprises a facilitating transfer material.

5. The method of claim 1, wherein establishing a spray of microdroplets comprises concentrating electrical charge on the coated particles as the microdroplet evaporates, and further wherein a space charge effect of the concentrated electrical charge substantially prevents agglomeration of the coated particles.

6. The method of claim 5, wherein the electrical charge concentrated on a coated particle is in the range of about 80 percent to about 95 percent of a maximum charge that is held by the microdroplet.

7. The method of claim 1, wherein the particles have a nominal diameter of about 2 nanometers to about 1 micron.

8. The method of claim 7, wherein the particles have a nominal diameter of about 10 nanometers to about 100 nanometers.

9. The method of claim 1, wherein the microdroplets have a nominal diameter of about 10 nanometers to about 10 microns and the particles have a nominal diameter of about 2 nanometers to about 1 micron.

10. The method of claim 1, wherein establishing the spray of microdroplets comprises establishing a continuous spray of coated particles.

11. The method of claim 1, wherein providing at least one opening at a spray dispenser end comprises providing at least two openings at the spray dispenser end, and further wherein flowing at least one liquid suspension comprising particles and a coating material through the opening comprises:
flowing a liquid suspension comprising particles through a first opening at the spray dispenser end; and
flowing a liquid suspension comprising coating material through a second opening at the spray dispenser end.

12. The method of claim 1, wherein the method further comprises controlling the amount of coating material in the microdroplets of the spray.

13. A method for coating particles, the method comprising:
providing a first flow of a suspension comprising at least particles, wherein the particles have a nominal diameter of about 2 nanometers to about 1 micron;
providing a second flow of a solution comprising a coating material; and
establishing a spray of substantially dispersed coated particles comprising separated particles of the first flow encapsulated by coating material of the second flow, the substantially dispersed coated particles having an electrical charge applied thereto such that a space charge effect resulting from repulsion of the electrically charged substantially dispersed coated particles is used to prevent agglomeration of the one or more substantially dispersed coated particles of the spray.

14. The method of claim 13, wherein the particles have a nominal diameter of about 10 nanometers to about 100 nanometers.

15. The method of claim 13, wherein establishing the spray of substantially dispersed coated particles comprises dispensing a spray of microdroplets suspending one or more particles, and further wherein the one or more particles are coated with at least a portion of the coating material and the electrical charge is concentrated on the coated particles as the microdroplets evaporates.

16. The method of claim 15, wherein the method further comprises controlling the amount of coating material in the microdroplets of the spray.

17. The method of claim 15, wherein the electrical charge concentrated on a coated particle is in the range of about 80 percent to about 95 percent of a maximum charge that is held by the microdroplet.

* * * * *

UNITED STATES PATENT AND TRADEMARK OFFICE
CERTIFICATE OF CORRECTION

PATENT NO. : 6,746,869 B2
DATED : June 8, 2004
INVENTOR(S) : David Y.H. Pui and Da-Ren Chen It is certified that error appears in the above-identified patent and that said Letters Patent is hereby corrected as shown below:

<u>Column 1,</u>
Line 7, delete "6,049,557" and insert -- 6,093,557 --.

<u>Column 22,</u>
Line 9, after "space" insert -- 487. --
Line 9, "The" should be the start of a new paragraph.

Signed and Sealed this

Thirtieth Day of November, 2004

JON W. DUDAS
*Director of the United States Patent and Trademark Office*